US012618092B2

(12) United States Patent
Horgan et al.

(10) Patent No.: US 12,618,092 B2
(45) Date of Patent: May 5, 2026

(54) METHOD AND APPARATUS FOR ENZYMATIC SYNTHESIS OF POLYNUCLEOTIDES

(71) Applicant: DNA Script, Le Kremlin-Bicêtre (FR)

(72) Inventors: Adrian Horgan, Le Kremlin-Bicêtre (FR); Xavier Godron, Le Kremlin-Bicêtre (FR)

(73) Assignee: DNA Script, Le Kremlin-Bicêtre (FR)

( * ) Notice: Subject to any disclaimer, the term of this patent is extended or adjusted under 35 U.S.C. 154(b) by 808 days.

(21) Appl. No.: 17/802,485

(22) PCT Filed: Feb. 22, 2021

(86) PCT No.: PCT/EP2021/054278
§ 371 (c)(1),
(2) Date: Aug. 25, 2022

(87) PCT Pub. No.: WO2021/170524
PCT Pub. Date: Sep. 2, 2021

(65) Prior Publication Data
US 2023/0089448 A1     Mar. 23, 2023

(30) Foreign Application Priority Data

Feb. 25, 2020    (EP) ..................................... 20159227

(51) Int. Cl.
*C12P 19/34*         (2006.01)
*B01J 19/00*         (2006.01)
*C12N 9/12*          (2006.01)
(52) U.S. Cl.
CPC ........... *C12P 19/34* (2013.01); *B01J 19/0046* (2013.01); *C12N 9/1264* (2013.01);
(Continued)

(58) Field of Classification Search
CPC .................. C12P 19/34; B01J 19/0046; B01J 2219/00585; B01J 2219/00587; C12N 9/1264
See application file for complete search history.

(56) References Cited

U.S. PATENT DOCUMENTS

| | | | |
|---|---|---|---|
| 5,273,718 A | 12/1993 | Skold et al. | |
| 5,367,066 A | 11/1994 | Urdea et al. | |

(Continued)

FOREIGN PATENT DOCUMENTS

| | | | |
|---|---|---|---|
| AU | 2018272302 A1 | 12/2019 | |
| CN | 109642255 A | 4/2019 | |

(Continued)

OTHER PUBLICATIONS

Becker et al. (1967) "The enzymatic cleavage of phosphate termini from polynucleotides", J. Biol. Chem., 242(5): 936-950.

(Continued)

*Primary Examiner* — Andrea Olson
(74) *Attorney, Agent, or Firm* — MORRISON & FOERSTER LLP

(57) ABSTRACT

The invention is directed to methods and apparatus for parallel enzymatic synthesis of polynucleotides in an array of reaction chambers using a template-free polymerase that has sequence-dependent coupling efficiencies. Whenever sequences causing low efficiency coupling occur at a 3' end of a growing chain of a polynucleotide being synthesized, one or more additional coupling cycles without de-protection steps are inserted into synthesis plans to provide additional time for completing the coupling reaction at that position of the polynucleotide.

9 Claims, 5 Drawing Sheets

Specification includes a Sequence Listing.

(52) U.S. Cl.
CPC ................. *B01J 2219/00423* (2013.01); *B01J
2219/00452* (2013.01); *B01J 2219/00695*
(2013.01); *B01J 2219/00722* (2013.01); *C12Y
207/07031* (2013.01)

(56) References Cited

U.S. PATENT DOCUMENTS

| | | | |
|---|---|---|---|
| 5,436,143 | A | 7/1995 | Hyman |
| 5,443,791 | A | 8/1995 | Cathcart et al. |
| 5,700,642 | A | 12/1997 | Monforte et al. |
| 5,739,386 | A | 4/1998 | Holmes |
| 5,763,594 | A | 6/1998 | Hiatt et al. |
| 5,808,045 | A | 9/1998 | Hiatt et al. |
| 5,830,655 | A | 11/1998 | Monforte et al. |
| 6,063,339 | A | 5/2000 | Tisone et al. |
| 7,057,026 | B2 | 6/2006 | Barnes et al. |
| 7,529,598 | B2 | 5/2009 | Ingenhoven et al. |
| 7,544,794 | B1 | 6/2009 | Benner |
| 8,212,020 | B2 | 7/2012 | Benner et al. |
| 8,580,197 | B2 | 11/2013 | Glauser et al. |
| 8,808,988 | B2 | 8/2014 | Zhao et al. |
| 9,103,809 | B2 | 8/2015 | West et al. |
| 10,435,676 | B2 | 10/2019 | Champion et al. |
| 2003/0086829 | A1* | 5/2003 | Livesay ............... B01J 19/0046 422/131 |
| 2003/0186226 | A1 | 10/2003 | Brennan et al. |
| 2004/0106728 | A1 | 6/2004 | McGall et al. |
| 2005/0037991 | A1 | 2/2005 | Bodepudi et al. |
| 2019/0078065 | A1* | 3/2019 | Baiga ................. C12N 15/1068 |
| 2019/0078126 | A1 | 3/2019 | Baiga et al. |
| 2019/0112627 | A1* | 4/2019 | Arlow .................... C07K 19/00 |
| 2022/0411840 | A1* | 12/2022 | Champion .............. C12P 19/34 |

FOREIGN PATENT DOCUMENTS

| | | | |
|---|---|---|---|
| WO | WO1991/006678 | 5/1991 | |
| WO | WO2004/005667 | 1/2004 | |
| WO | WO2014/179596 | 11/2014 | |
| WO | WO2015/159023 | 10/2015 | |
| WO | WO2017/216472 | 12/2017 | |
| WO | WO2018/215803 | 11/2018 | |
| WO | WO2018/222853 | 12/2018 | |
| WO | WO2019/135007 | 7/2019 | |
| WO | WO-2019150134 A1 * | 8/2019 | .............. C12P 19/34 |

OTHER PUBLICATIONS

Butendeich et al. (2013) "Evaluation of a Liquid Dispenser for Assay Development and Enxymology in I536-Will Format", J. Laboratory Automation, 18(3): 245-250.

Cameron et al. (1977) "3'-phosphatase activity in T4 polynucleotide kinase", Biochemistry, 16(23): 5120-5126.

Canard et al. (1994) "DNA polymerase fluorescent substrates with reversible 3'-tags", Gene, 148: 1-6.

Canard et al. (1995) "Catalytic editing properties of DNA polymerases", Proc. Natl. Acad. Sci., 92: 10859-10863.

Cheng et al. (2002) "High throughput parallel synthesis of oligonucleotides with 1536 channel synthesizer", Nucleic Acids Research, 30(18): e93.

Delarue et al., (2002) "Crystal structures of a template-independent DNA polymerase: Murine terminal deoxynucleotidyltransferase", EMBO J., 21: 427-439.

Ferrero et al. (2000) "Chemoenzymatic transformations in nucleoside chemistry", Monatshefte fur Chemie, 131: 585-616.

Grantham (1974) "Amino Acid Difference Formula to Help Explain Protein Evolution", Science, 185: 862-864.

Guo et al, (2008) "Four-color DNA sequencing with 3'-O-modified nucleotide reversible terminators and chemically cleavable fluorescent dideoxynucleotides", Proc. Natl. Acad. Sci., 105 (27): 9145-9150.

Jensen et al. (2018) "Template-Independent Enzymatic 11 Oligonucleotide Synthesis (TiEOS): Its History, Prospects, and Challenges", Biochemistry, 57: 1821-1832.

Mathews et al. (2016) "Photo-cleavable nucleotides for primer free enzyme mediated DNA synthesis", Organic & Biomolecular Chemistry, 14: 8278-8288.

Meng et al. (2006) "Design and Synthesis of a Photocleavable Fluorescent Nucleotide 3'-O-Allyl-dGTP-PC-Bodipy-FL-510 as a Reversible Terminator for DNA Sequencing by Synthesis", J. Org. Chem., 14: 3248-3252.

Metzker et al. (1994) "Termination of DNA synthesis by novel 3'-modifieddeoxyribonucleoside 5'-triphosphates", Nucleic Acids Research, 22: 4259-4267.

Motea et al. (2010) "Terminal Deoxynucleotidyl Transferase: The Story of a Misguided DNA Polymerase", Biochim. Biophys. Acta, 1804(5): 1151-1166.

Rasolonjatovo et al. (1999) "Development of a new sequencing method: 3'-ester cleavage catalyzed by Taq DNA polymerase", Nucleosides & Nucleotides, 18(4&5): 1021-1022.

Schmitz et al. (1999) "Solid-Phase Enzymatic Synthesis of Oligonucleotides", Organic Lett., 1(11): 1729-1731.

Sindelar et al. (1995) "High-throughput DNA synthesis in a multichannel format", Nucleic Acids Research, 23 (6): 982-987.

Taunton-Rigby et al. (1973) "Oligonucleotide synthesis. III. Enzymically removable acyl protecting groups", J. Org. Chem., 38(5): 977-985.

Uemura et al. (1989) "Regioselective deprotection of 3', 5'-O-acylated pyrimidine nucleosides by lipase and esterase", 9 Tetrahedron Lett., 30(29): 3819-3820.

* cited by examiner

SEQUENCE LISTING

<160> NUMBER OF SEQ ID NOS: 30

<210> SEQ ID NO 1
<211> LENGTH: 21
<212> TYPE: DNA

<213> ORGANISM: ARTIFICIAL SEQUENCE
<220> FEATURE:
<223> OTHER INFORMATION: nucleotide

<400> SEQUENCE: 1
gtttcctaag ttgcatttgc g                                                          21

<210> SEQ ID NO 2
<211> LENGTH: 381
<212> TYPE: PRT
<213> ORGANISM: ARTIFICIAL SEQUENCE
<220> FEATURE:
<223> OTHER INFORMATION: truncated mouse TdT

<400> SEQUENCE: 2

Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Leu Arg Glu Asn Glu Gly Ser Cys Leu Ala Phe Met Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
            260                 265                 270

Gln Lys Cys Phe Leu Ile Leu Lys Leu Asp His Gly Arg Val His Ser
        275                 280                 285

Glu Lys Ser Gly Gln Gln Glu Gly Lys Gly Trp Lys Ala Ile Arg Val
    290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr

-continued

```
                    325                 330                 335
His Glu Arg Lys Met Met Leu Asp Asn His Ala Leu Tyr Asp Arg Thr
            340                 345                 350

Lys Arg Val Phe Leu Glu Ala Glu Ser Glu Glu Glu Ile Phe Ala His
        355                 360                 365

Leu Gly Leu Asp Tyr Ile Glu Pro Trp Glu Arg Asn Ala
    370                 375                 380

<210> SEQ ID NO 3
<211> LENGTH: 380
<212> TYPE: PRT
<213> ORGANISM: BOVINE

<400> SEQUENCE: 3

Asp Tyr Ser Ala Thr Pro Asn Pro Gly Phe Gln Lys Thr Pro Pro Leu
1               5                   10                  15

Ala Val Lys Lys Ile Ser Gln Tyr Ala Cys Gln Arg Lys Thr Thr Leu
            20                  25                  30

Asn Asn Tyr Asn His Ile Phe Thr Asp Ala Phe Glu Ile Leu Ala Glu
        35                  40                  45

Asn Ser Glu Phe Lys Glu Asn Glu Val Ser Tyr Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Lys Val Lys Cys Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Ser
    130                 135                 140

Leu Ser Lys Ile Met Ser Asp Lys Thr Leu Lys Phe Thr Lys Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
            180                 185                 190

Phe Leu Pro Asp Ala Phe Val Thr Met Thr Gly Gly Phe Arg Arg Gly
        195                 200                 205

Lys Lys Ile Gly His Asp Val Asp Phe Leu Ile Thr Ser Pro Gly Ser
    210                 215                 220

Ala Glu Asp Glu Glu Gln Leu Leu Pro Lys Val Ile Asn Leu Trp Glu
225                 230                 235                 240

Lys Lys Gly Leu Leu Leu Tyr Tyr Asp Leu Val Glu Ser Thr Phe Glu
                245                 250                 255

Lys Phe Lys Leu Pro Ser Arg Gln Val Asp Thr Leu Asp His Phe Gln
            260                 265                 270

Lys Cys Phe Leu Ile Leu Lys Leu His His Gln Arg Val Asp Ser Ser
        275                 280                 285

Lys Ser Asn Gln Gln Glu Gly Lys Thr Trp Lys Ala Ile Arg Val Asp
    290                 295                 300

Leu Val Met Cys Pro Tyr Glu Asn Arg Ala Phe Ala Leu Leu Gly Trp
305                 310                 315                 320
```

-continued

```
Thr Gly Ser Arg Gln Phe Glu Arg Asp Ile Arg Arg Tyr Ala Thr His
                325                 330                 335

Glu Arg Lys Met Met Leu Asp Asn His Ala Leu Tyr Asp Lys Thr Lys
            340                 345                 350

Arg Val Phe Leu Lys Ala Glu Ser Glu Glu Glu Ile Phe Ala His Leu
        355                 360                 365

Gly Leu Asp Tyr Ile Glu Pro Trp Glu Arg Asn Ala
    370                 375                 380

<210> SEQ ID NO 4
<211> LENGTH: 380
<212> TYPE: PRT
<213> ORGANISM: HUMAN

<400> SEQUENCE: 4

Asp Tyr Ser Asp Ser Thr Asn Pro Gly Pro Pro Lys Thr Pro Pro Ile
1               5                   10                  15

Ala Val Gln Lys Ile Ser Gln Tyr Ala Cys Gln Arg Arg Thr Thr Leu
            20                  25                  30

Asn Asn Cys Asn Gln Ile Phe Thr Asp Ala Phe Asp Ile Leu Ala Glu
        35                  40                  45

Asn Cys Glu Phe Arg Glu Asn Glu Asp Ser Cys Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Ser Lys Val Lys Gly Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Ser Lys Val Arg Ser Asp Lys Ser Leu Lys Phe Thr Arg Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Ser Val Leu Val Lys Glu Ala Val Trp Ala
            180                 185                 190

Phe Leu Pro Asp Ala Phe Val Thr Met Thr Gly Gly Phe Arg Arg Gly
        195                 200                 205

Lys Lys Met Gly His Asp Val Asp Phe Leu Ile Thr Ser Pro Gly Ser
    210                 215                 220

Thr Glu Asp Glu Glu Gln Leu Leu Gln Lys Val Met Asn Leu Trp Glu
225                 230                 235                 240

Lys Lys Gly Leu Leu Leu Tyr Tyr Asp Leu Val Glu Ser Thr Phe Glu
                245                 250                 255

Lys Leu Arg Leu Pro Ser Arg Lys Val Asp Ala Leu Asp His Phe Gln
            260                 265                 270

Lys Cys Phe Leu Ile Phe Lys Leu Pro Arg Gln Arg Val Asp Ser Asp
        275                 280                 285

Gln Ser Ser Trp Gln Glu Gly Lys Thr Trp Lys Ala Ile Arg Val Asp
    290                 295                 300

Leu Val Leu Cys Pro Tyr Glu Arg Arg Ala Phe Ala Leu Leu Gly Trp
305                 310                 315                 320
```

-continued

```
Thr Gly Ser Arg Gln Phe Glu Arg Asp Leu Arg Arg Tyr Ala Thr His
                325                 330                 335

Glu Arg Lys Met Ile Leu Asp Asn His Ala Leu Tyr Asp Lys Thr Lys
                340                 345                 350

Arg Ile Phe Leu Lys Ala Glu Ser Glu Glu Glu Ile Phe Ala His Leu
                355                 360                 365

Gly Leu Asp Tyr Ile Glu Pro Trp Glu Arg Asn Ala
    370                 375                 380

<210> SEQ ID NO 5
<211> LENGTH: 376
<212> TYPE: PRT
<213> ORGANISM: CHICKEN

<400> SEQUENCE: 5

Gln Tyr Pro Thr Leu Lys Thr Pro Glu Ser Glu Val Ser Ser Phe Thr
1               5                   10                  15

Ala Ser Lys Val Ser Gln Tyr Ser Cys Gln Arg Lys Thr Thr Leu Asn
                20                  25                  30

Asn Cys Asn Lys Lys Phe Thr Asp Ala Phe Glu Ile Met Ala Glu Asn
            35                  40                  45

Tyr Glu Phe Lys Glu Asn Glu Ile Phe Cys Leu Glu Phe Leu Arg Ala
    50                  55                  60

Ala Ser Val Leu Lys Ser Leu Pro Phe Pro Val Thr Arg Met Lys Asp
65                  70                  75                  80

Ile Gln Gly Leu Pro Cys Met Gly Asp Arg Val Arg Asp Val Ile Glu
                85                  90                  95

Glu Ile Ile Glu Glu Gly Glu Ser Ser Arg Ala Lys Asp Val Leu Asn
                100                 105                 110

Asp Glu Arg Tyr Lys Ser Phe Lys Glu Phe Thr Ser Val Phe Gly Val
            115                 120                 125

Gly Val Lys Thr Ser Glu Lys Trp Phe Arg Met Gly Leu Arg Thr Val
    130                 135                 140

Glu Glu Val Lys Ala Asp Lys Thr Leu Lys Leu Ser Lys Met Gln Arg
145                 150                 155                 160

Ala Gly Phe Leu Tyr Tyr Glu Asp Leu Val Ser Cys Val Ser Lys Ala
                165                 170                 175

Glu Ala Asp Ala Val Ser Ser Ile Val Lys Asn Thr Val Cys Thr Phe
                180                 185                 190

Leu Pro Asp Ala Leu Val Thr Ile Thr Gly Gly Phe Arg Arg Gly Lys
            195                 200                 205

Lys Ile Gly His Asp Ile Asp Phe Leu Ile Thr Ser Pro Gly Gln Arg
    210                 215                 220

Glu Asp Asp Glu Leu Leu His Lys Gly Leu Leu Leu Tyr Cys Asp Ile
225                 230                 235                 240

Ile Glu Ser Thr Phe Val Lys Glu Gln Ile Pro Ser Arg His Val Asp
                245                 250                 255

Ala Met Asp His Phe Gln Lys Cys Phe Ala Ile Leu Lys Leu Tyr Gln
            260                 265                 270

Pro Arg Val Asp Asn Ser Ser Tyr Asn Met Ser Lys Lys Cys Asp Met
            275                 280                 285

Ala Glu Val Lys Asp Trp Lys Ala Ile Arg Val Asp Leu Val Ile Thr
    290                 295                 300

Pro Phe Glu Gln Tyr Ala Tyr Ala Leu Leu Gly Trp Thr Gly Ser Arg
```

-continued

```
        305                 310                 315                 320

Gln Phe Gly Arg Asp Leu Arg Arg Tyr Ala Thr His Glu Arg Lys Met
                325                 330                 335

Met Leu Asp Asn His Ala Leu Tyr Asp Lys Arg Lys Arg Val Phe Leu
            340                 345                 350

Lys Ala Gly Ser Glu Glu Glu Ile Phe Ala His Leu Gly Leu Asp Tyr
            355                 360                 365

Val Glu Pro Trp Glu Arg Asn Ala
        370                 375

<210> SEQ ID NO 6
<211> LENGTH: 387
<212> TYPE: PRT
<213> ORGANISM: POSSUM

<400> SEQUENCE: 6

Ser Ala Asn Pro Asp Pro Thr Ala Gly Thr Leu Asn Ile Leu Pro Pro
1               5                   10                  15

Thr Thr Lys Thr Ile Ser Gln Tyr Ala Cys Gln Arg Arg Thr Thr Ile
            20                  25                  30

Asn Asn His Asn Gln Arg Phe Thr Asp Ala Phe Glu Ile Leu Ala Lys
            35                  40                  45

Asn Tyr Glu Phe Lys Glu Asn Asp Asp Thr Cys Leu Thr Phe Met Arg
        50                  55                  60

Ala Ile Ser Val Leu Lys Cys Leu Pro Phe Glu Val Val Ser Leu Lys
65                  70                  75                  80

Asp Thr Glu Gly Leu Pro Trp Ile Gly Asp Glu Val Lys Gly Ile Met
                85                  90                  95

Glu Glu Ile Ile Glu Asp Gly Glu Ser Leu Glu Val Gln Ala Val Leu
            100                 105                 110

Asn Asp Glu Arg Tyr Gln Ser Phe Lys Leu Phe Thr Ser Val Phe Gly
            115                 120                 125

Val Gly Leu Lys Thr Ala Asp Lys Trp Tyr Arg Met Gly Phe Arg Thr
        130                 135                 140

Leu Asn Lys Ile Arg Ser Asp Lys Thr Leu Lys Leu Thr Lys Met Gln
145                 150                 155                 160

Lys Ala Gly Leu Cys Tyr Tyr Glu Asp Leu Ile Asp Cys Val Ser Lys
                165                 170                 175

Ala Glu Ala Asp Ala Val Ser Leu Leu Val Gln Asp Ala Val Trp Thr
            180                 185                 190

Phe Leu Pro Asp Ala Leu Val Thr Ile Thr Gly Gly Phe Arg Arg Gly
            195                 200                 205

Lys Glu Phe Gly His Asp Val Asp Phe Leu Ile Thr Ser Pro Gly Ala
        210                 215                 220

Glu Lys Glu Gln Glu Asp Gln Leu Leu Gln Lys Val Thr Asn Leu Trp
225                 230                 235                 240

Lys Lys Gln Gly Leu Leu Leu Tyr Cys Asp Leu Ile Glu Ser Thr Phe
                245                 250                 255

Glu Asp Leu Lys Leu Pro Ser Arg Lys Ile Asp Ala Leu Asp His Phe
            260                 265                 270

Gln Lys Cys Phe Leu Ile Leu Lys Leu Tyr His His Lys Glu Asp Lys
        275                 280                 285

Arg Lys Trp Glu Met Pro Thr Gly Ser Asn Glu Ser Glu Ala Lys Ser
        290                 295                 300
```

-continued

```
Trp Lys Ala Ile Arg Val Asp Leu Val Val Cys Pro Tyr Asp Arg Tyr
305                 310                 315                 320

Ala Phe Ala Leu Leu Gly Trp Ser Gly Ser Arg Gln Phe Glu Arg Asp
                325                 330                 335

Leu Arg Arg Tyr Ala Thr His Glu Lys Lys Met Met Leu Asp Asn His
                340                 345                 350

Ala Leu Tyr Asp Lys Thr Lys Lys Ile Phe Leu Lys Ala Lys Ser Glu
                355                 360                 365

Glu Glu Ile Phe Ala His Leu Gly Leu Glu Tyr Ile Gln Pro Ser Glu
        370                 375                 380

Arg Asn Ala
385

<210> SEQ ID NO 7
<211> LENGTH: 381
<212> TYPE: PRT
<213> ORGANISM: SHREW

<400> SEQUENCE: 7

Asp Cys Pro Ala Ser His Asp Ser Ser Pro Gln Lys Thr Glu Ser Ala
1               5                   10                  15

Ala Val Gln Lys Ile Ser Gln Tyr Ala Cys Gln Arg Arg Thr Thr Leu
                20                  25                  30

Asn Asn His Asn His Ile Phe Thr Asp Ala Phe Glu Ile Leu Ala Glu
                35                  40                  45

Asn Cys Glu Phe Arg Glu Asn Glu Gly Ser Tyr Val Thr Tyr Met Arg
        50                  55                  60

Ala Ala Ser Val Leu Lys Ser Leu Pro Phe Ser Ile Ile Ser Met Lys
65                  70                  75                  80

Asp Thr Glu Gly Ile Pro Cys Leu Ala Asp Lys Val Lys Cys Val Ile
                85                  90                  95

Glu Glu Ile Ile Glu Asp Gly Glu Ser Ser Glu Val Lys Ala Val Leu
                100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Leu Gly Phe Arg Thr
        130                 135                 140

Leu Ser Gly Ile Met Asn Asp Lys Thr Leu Lys Leu Thr His Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
                180                 185                 190

Phe Leu Pro Asp Ala Ile Val Thr Met Thr Gly Gly Phe Arg Arg Gly
        195                 200                 205

Lys Lys Val Gly His Asp Val Asp Phe Leu Ile Thr Ser Pro Glu Ala
        210                 215                 220

Thr Glu Glu Gln Glu Gln Gln Leu Leu His Lys Val Ile Thr Phe Trp
225                 230                 235                 240

Glu Lys Glu Gly Leu Leu Leu Tyr Cys Asp Leu Tyr Glu Ser Thr Phe
                245                 250                 255

Glu Lys Leu Lys Met Pro Ser Arg Lys Val Asp Ala Leu Asp His Phe
                260                 265                 270

Gln Lys Cys Phe Leu Ile Leu Lys Leu His Arg Glu Cys Val Asp Asp
        275                 280                 285
```

-continued

```
Gly Thr Ser Ser Gln Leu Gln Gly Lys Thr Trp Lys Ala Ile Arg Val
    290                 295                 300

Asp Leu Val Val Cys Pro Tyr Glu Cys Arg Ala Phe Ala Leu Leu Gly
305                 310                 315                 320

Trp Thr Gly Ser Pro Gln Phe Glu Arg Asp Leu Arg Arg Tyr Ala Thr
                325                 330                 335

His Glu Arg Lys Met Met Leu Asp Asn His Ala Leu Tyr Asp Lys Thr
                340                 345                 350

Lys Arg Lys Phe Leu Ser Ala Asp Ser Glu Glu Asp Ile Phe Ala His
                355                 360                 365

Leu Gly Leu Asp Tyr Ile Glu Pro Trp Glu Arg Asn Ala
    370                 375                 380

<210> SEQ ID NO 8
<211> LENGTH: 387
<212> TYPE: PRT
<213> ORGANISM: PYTHON

<400> SEQUENCE: 8

Glu Lys Tyr Gln Leu Pro Glu Asp Glu Asp Arg Ser Val Thr Ser Asp
1                   5                   10                  15

Leu Asp Arg Asp Ser Ile Ser Glu Tyr Ala Cys Gln Arg Arg Thr Thr
                20                  25                  30

Leu Lys Asn Tyr Asn Gln Lys Phe Thr Asp Ala Phe Glu Ile Leu Ala
            35                  40                  45

Glu Asn Tyr Glu Phe Asn Glu Asn Lys Gly Phe Cys Thr Ala Phe Arg
    50                  55                  60

Arg Ala Ala Ser Val Leu Lys Cys Leu Pro Phe Thr Ile Val Gln Val
65                  70                  75                  80

His Asp Ile Glu Gly Val Pro Trp Met Gly Lys Gln Val Lys Gly Ile
                85                  90                  95

Ile Glu Asp Ile Ile Glu Glu Gly Glu Ser Ser Lys Val Lys Ala Val
            100                 105                 110

Leu Asp Asn Glu Asn Tyr Arg Ser Val Lys Leu Phe Thr Ser Val Phe
            115                 120                 125

Gly Val Gly Leu Lys Thr Ser Asp Lys Trp Tyr Arg Met Gly Leu Arg
    130                 135                 140

Thr Leu Glu Glu Val Lys Arg Asp Lys Asn Leu Lys Leu Thr Arg Met
145                 150                 155                 160

Gln Lys Ala Gly Phe Leu His Tyr Asp Asp Leu Thr Ser Cys Val Ser
            165                 170                 175

Lys Ala Glu Ala Asp Ala Ala Ser Leu Ile Val Gln Asp Val Val Trp
            180                 185                 190

Lys Ile Val Pro Asn Ala Ile Val Thr Ile Ala Gly Gly Phe Arg Arg
            195                 200                 205

Gly Lys Gln Thr Gly His Asp Val Asp Phe Leu Ile Thr Val Pro Gly
    210                 215                 220

Ser Lys Gln Glu Glu Glu Glu Leu Leu His Thr Val Ile Asp Ile Trp
225                 230                 235                 240

Lys Lys Gln Glu Leu Leu Leu Tyr Tyr Asp Leu Ile Glu Ser Thr Phe
                245                 250                 255

Glu Asp Thr Lys Leu Pro Ser Arg Lys Val Asp Ala Leu Asp His Phe
                260                 265                 270

Gln Lys Cys Phe Ala Ile Leu Lys Val His Lys Glu Arg Glu Asp Lys
```

-continued

```
            275                 280                 285
Gly Asn Ser Ile Arg Ser Lys Ala Phe Ser Glu Glu Glu Ile Lys Asp
    290                 295                 300

Trp Lys Ala Ile Arg Val Asp Leu Val Val Val Pro Phe Glu Gln Tyr
305                 310                 315                 320

Ala Phe Ala Leu Leu Gly Trp Thr Gly Ser Thr Gln Phe Glu Arg Asp
            325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Asn Ala Ala Ser Glu
            355                 360                 365

Glu Glu Ile Phe Ala His Leu Gly Leu Asp Tyr Leu Glu Pro Trp Glu
    370                 375                 380

Arg Asn Ala
385

<210> SEQ ID NO 9
<211> LENGTH: 381
<212> TYPE: PRT
<213> ORGANISM: DOG

<400> SEQUENCE: 9

Asp Tyr Thr Ala Ser Pro Asn Pro Glu Leu Gln Lys Thr Leu Pro Val
1               5                   10                  15

Ala Val Lys Lys Ile Ser Gln Tyr Ala Cys Gln Arg Arg Thr Thr Leu
            20                  25                  30

Asn Asn Tyr Asn Asn Val Phe Thr Asp Ala Phe Glu Val Leu Ala Glu
            35                  40                  45

Asn Tyr Glu Phe Arg Glu Asn Glu Val Phe Ser Leu Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Gln Val Lys Cys Ile Ile
            85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Thr
    130                 135                 140

Leu Ser Lys Ile Lys Ser Asp Lys Ser Leu Lys Phe Thr Pro Met Gln
145                 150                 155                 160

Lys Ala Gly Phe Leu Tyr Tyr Glu Asp Leu Val Ser Cys Val Thr Arg
            165                 170                 175

Ala Glu Ala Glu Ala Val Gly Val Leu Val Lys Glu Ala Val Gly Ala
            180                 185                 190

Phe Leu Pro Asp Ala Phe Val Thr Met Thr Gly Gly Phe Arg Arg Gly
            195                 200                 205

Lys Lys Met Gly His Asp Val Asp Phe Leu Ile Thr Ser Pro Gly Ser
    210                 215                 220

Thr Asp Glu Asp Glu Glu Gln Leu Leu Pro Lys Val Ile Asn Leu Trp
225                 230                 235                 240

Glu Arg Lys Gly Leu Leu Leu Tyr Cys Asp Leu Val Glu Ser Thr Phe
            245                 250                 255
```

-continued

Glu Lys Leu Lys Leu Pro Ser Arg Lys Val Asp Ala Leu Asp His Phe
                260                 265                 270

Gln Lys Cys Phe Leu Ile Leu Lys Leu His His Gln Arg Val Asp Gly
        275                 280                 285

Gly Lys Cys Ser Gln Gln Glu Gly Lys Thr Trp Lys Ala Ile Arg Val
        290                 295                 300

Asp Leu Val Met Cys Pro Tyr Glu Arg Arg Ala Phe Ala Leu Leu Gly
305                 310                 315                 320

Trp Thr Gly Ser Arg Gln Phe Glu Arg Asp Leu Arg Arg Tyr Ala Ser
                325                 330                 335

His Glu Arg Lys Met Ile Leu Asp Asn His Ala Leu Tyr Asp Lys Thr
                340                 345                 350

Lys Lys Ile Phe Leu Lys Ala Glu Ser Glu Glu Glu Ile Phe Ala His
        355                 360                 365

Leu Gly Leu Asp Tyr Ile Glu Pro Trp Glu Arg Asn Ala
        370                 375                 380

<210> SEQ ID NO 10
<211> LENGTH: 382
<212> TYPE: PRT
<213> ORGANISM: TRUNC MOLE

<400> SEQUENCE: 10

Gly Asp Cys Pro Ala Ser His Asp Ser Ser Pro Gln Lys Thr Glu Ser
1               5                   10                  15

Ala Ala Val Gln Lys Ile Ser Gln Tyr Ala Cys Gln Arg Arg Thr Thr
                20                  25                  30

Leu Asn Asn His Asn His Ile Phe Thr Asp Ala Phe Glu Ile Leu Ala
        35                  40                  45

Glu Asn Cys Glu Phe Arg Glu Asn Glu Gly Ser Tyr Val Thr Tyr Met
        50                  55                  60

Arg Ala Ala Ser Val Leu Lys Ser Leu Pro Phe Ser Ile Ile Ser Met
65              70                  75                  80

Lys Asp Thr Glu Gly Ile Pro Cys Leu Ala Asp Lys Val Lys Cys Val
                85                  90                  95

Ile Glu Glu Ile Ile Glu Asp Gly Glu Ser Ser Glu Val Lys Ala Val
                100                 105                 110

Leu Asn Asp Glu Arg Tyr Lys Ser Phe Lys Leu Phe Thr Ser Val Phe
        115                 120                 125

Gly Val Gly Leu Lys Thr Ala Glu Lys Trp Phe Arg Leu Gly Phe Arg
        130                 135                 140

Thr Leu Ser Gly Ile Met Asn Asp Lys Thr Leu Lys Leu Thr His Met
145                 150                 155                 160

Gln Lys Ala Gly Phe Leu Tyr Tyr Glu Asp Leu Val Ser Cys Val Thr
                165                 170                 175

Arg Ala Glu Ala Glu Ala Val Gly Val Leu Val Lys Glu Ala Val Trp
                180                 185                 190

Ala Phe Leu Pro Asp Ala Ile Val Thr Met Thr Gly Gly Phe Arg Arg
        195                 200                 205

Gly Lys Lys Val Gly His Asp Val Asp Phe Leu Ile Thr Ser Pro Glu
        210                 215                 220

Ala Thr Glu Glu Gln Glu Gln Gln Leu Leu His Lys Val Ile Thr Phe
225                 230                 235                 240

Trp Glu Lys Glu Gly Leu Leu Leu Tyr Cys Asp Leu Tyr Glu Ser Thr
                245                 250                 255

-continued

```
Phe Glu Lys Leu Lys Met Pro Ser Arg Lys Val Asp Ala Leu Asp His
        260                 265                 270

Phe Gln Lys Cys Phe Leu Ile Leu Lys Leu His Arg Glu Cys Val Asp
        275                 280                 285

Asp Gly Thr Ser Ser Gln Leu Gln Gly Lys Thr Trp Lys Ala Ile Arg
        290                 295                 300

Val Asp Leu Val Val Cys Pro Tyr Glu Cys Arg Ala Phe Ala Leu Leu
305                 310                 315                 320

Gly Trp Thr Gly Ser Pro Gln Phe Glu Arg Asp Leu Arg Arg Tyr Ala
                325                 330                 335

Thr His Glu Arg Lys Met Met Leu Asp Asn His Ala Leu Tyr Asp Lys
        340                 345                 350

Thr Lys Arg Lys Phe Leu Ser Ala Asp Ser Glu Glu Asp Ile Phe Ala
        355                 360                 365

His Leu Gly Leu Asp Tyr Ile Glu Pro Trp Glu Arg Asn Ala
    370                 375                 380

<210> SEQ ID NO 11
<211> LENGTH: 379
<212> TYPE: PRT
<213> ORGANISM: PIKA TRUNK

<400> SEQUENCE: 11

Glu Tyr Ser Ala Asn Pro Ser Pro Gly Pro Gln Ala Thr Pro Ala Val
1                   5                   10                  15

Tyr Lys Ile Ser Gln Tyr Ala Cys Gln Arg Arg Thr Thr Leu Asn Asn
            20                  25                  30

His Asn His Ile Phe Thr Asp Ala Phe Glu Ile Leu Ala Glu Asn Tyr
        35                  40                  45

Glu Phe Lys Glu Asn Glu Gly Cys Tyr Val Thr Tyr Met Arg Ala Ala
    50                  55                  60

Ser Val Leu Lys Ser Leu Pro Phe Thr Ile Val Ser Met Lys Asp Thr
65                  70                  75                  80

Glu Gly Ile Pro Cys Leu Glu Asp Lys Val Lys Ser Ile Met Glu Glu
                85                  90                  95

Ile Ile Glu Glu Gly Glu Ser Ser Glu Val Lys Ala Val Leu Ser Asp
            100                 105                 110

Glu Arg Tyr Gln Cys Phe Lys Leu Phe Thr Ser Val Phe Gly Val Gly
        115                 120                 125

Leu Lys Thr Ser Glu Lys Trp Phe Arg Met Gly Phe Arg Ser Leu Ser
        130                 135                 140

Asn Ile Arg Leu Asp Lys Ser Leu Lys Phe Thr Gln Met Gln Lys Ala
145                 150                 155                 160

Gly Phe Arg Tyr Tyr Glu Asp Ile Val Ser Cys Val Thr Arg Ala Glu
                165                 170                 175

Ala Glu Ala Val Asp Val Leu Val Asn Glu Ala Val Arg Ala Phe Leu
            180                 185                 190

Pro Asp Ala Phe Ile Thr Met Thr Gly Gly Phe Arg Arg Gly Lys Lys
        195                 200                 205

Ile Gly His Asp Val Asp Phe Leu Ile Thr Ser Pro Glu Leu Thr Glu
    210                 215                 220

Glu Asp Glu Gln Gln Leu Leu His Lys Val Met Asn Leu Trp Glu Lys
225                 230                 235                 240

Lys Gly Leu Leu Leu Tyr His Asp Leu Val Glu Ser Thr Phe Glu Lys
```

-continued

```
                    245                 250                 255

Leu Lys Gln Pro Ser Arg Lys Val Asp Ala Leu Asp His Phe Gln Lys
            260                 265                 270

Cys Phe Leu Ile Phe Lys Leu Tyr His Glu Arg Val Gly Gly Asp Arg
            275                 280                 285

Cys Arg Gln Pro Glu Gly Lys Asp Trp Lys Ala Ile Arg Val Asp Leu
            290                 295                 300

Val Met Cys Pro Tyr Glu Cys His Ala Phe Ala Leu Leu Gly Trp Thr
305                 310                 315                 320

Gly Ser Arg Gln Phe Glu Arg Asp Leu Arg Arg Tyr Ala Ser His Glu
                    325                 330                 335

Arg Lys Met Ile Leu Asp Asn His Ala Leu Tyr Asp Lys Thr Lys Arg
                    340                 345                 350

Val Phe Leu Gln Ala Glu Asn Glu Glu Glu Ile Phe Ala His Leu Gly
            355                 360                 365

Leu Asp Tyr Ile Glu Pro Trp Glu Arg Asn Ala
    370                 375

<210> SEQ ID NO 12
<211> LENGTH: 384
<212> TYPE: PRT
<213> ORGANISM: TRUNC HEDGEHOG

<400> SEQUENCE: 12

Asp Ala Ser Phe Gly Ser Asn Pro Gly Ser Gln Asn Thr Pro Pro Leu
1               5                   10                  15

Ala Ile Lys Lys Ile Ser Gln Tyr Ala Cys Gln Arg Arg Thr Ser Leu
            20                  25                  30

Asn Asn Cys Asn His Ile Phe Thr Asp Ala Leu Asp Ile Leu Ala Glu
            35                  40                  45

Asn His Glu Phe Arg Glu Asn Glu Val Ser Cys Val Ala Phe Met Arg
    50                  55                  60

Ala Ala Ser Val Leu Lys Ser Leu Pro Phe Thr Ile Ile Ser Met Lys
65                  70                  75                  80

Asp Thr Lys Gly Ile Pro Cys Leu Gly Asp Lys Ala Lys Cys Val Ile
                85                  90                  95

Glu Glu Ile Ile Glu Asp Gly Glu Ser Ser Glu Val Lys Ala Ile Leu
            100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Thr
    130                 135                 140

Leu Asn Lys Ile Met Ser Asp Lys Thr Leu Lys Leu Thr Arg Met Gln
145                 150                 155                 160

Lys Ala Gly Phe Leu Tyr Tyr Glu Asp Leu Val Ser Cys Val Ala Lys
                165                 170                 175

Ala Glu Ala Asp Ala Val Ser Val Leu Val Gln Glu Ala Val Trp Ala
            180                 185                 190

Phe Leu Pro Asp Ala Met Val Thr Met Thr Gly Gly Phe Arg Arg Gly
            195                 200                 205

Lys Lys Leu Gly His Asp Val Asp Phe Leu Ile Thr Ser Pro Gly Ala
    210                 215                 220

Thr Glu Glu Glu Glu Gln Gln Leu Leu Pro Lys Val Ile Asn Phe Trp
225                 230                 235                 240
```

```
Glu Arg Lys Gly Leu Leu Leu Tyr His Asp Leu Val Glu Ser Thr Phe
            245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His Leu Gln His Val Asn Gly
            275                 280                 285

Val Gly Asn Ser Lys Thr Gly Gln Gln Glu Gly Lys Asn Trp Lys Ala
        290                 295                 300

Ile Arg Val Asp Leu Val Met Cys Pro Tyr Glu Arg Arg Ala Phe Ala
305                 310                 315                 320

Leu Leu Gly Trp Thr Gly Ser Arg Gln Phe Glu Arg Asp Leu Arg Arg
                325                 330                 335

Phe Ala Thr His Glu Arg Lys Met Met Leu Asp Asn His Ala Leu Tyr
                340                 345                 350

Asp Lys Thr Lys Arg Ile Phe Leu Lys Ala Glu Ser Glu Glu Glu Ile
            355                 360                 365

Phe Ala His Leu Gly Leu Asp Tyr Ile Asp Pro Trp Glu Arg Asn Ala
        370                 375                 380

<210> SEQ ID NO 13
<211> LENGTH: 381
<212> TYPE: PRT
<213> ORGANISM: TREE SHREW

<400> SEQUENCE: 13

Asp His Ser Thr Ser Pro Ser Pro Gly Pro Gln Lys Thr Pro Ala Leu
1               5                   10                  15

Ala Val Gln Lys Ile Ser Gln Tyr Ala Cys Gln Arg Arg Thr Thr Leu
            20                  25                  30

Asn Asn Cys Asn Arg Val Phe Thr Asp Ala Phe Glu Thr Leu Ala Glu
        35                  40                  45

Asn Tyr Glu Phe Arg Glu Asn Glu Asp Ser Ser Val Ile Phe Leu Arg
    50                  55                  60

Ala Ala Ser Val Leu Arg Ser Leu Pro Phe Thr Ile Thr Ser Met Arg
65                  70                  75                  80

Asp Thr Glu Gly Leu Pro Cys Leu Gly Asp Lys Val Lys Cys Val Ile
                85                  90                  95

Glu Glu Ile Ile Glu Asp Gly Glu Ser Ser Glu Val Asn Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Ser Arg Val Arg Ser Asp Lys Ser Leu His Leu Thr Arg Met Gln
145                 150                 155                 160

Gln Ala Gly Phe Leu Tyr Tyr Glu Asp Leu Ala Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Leu Val Thr Ile Thr Gly Gly Phe Arg Arg Gly
        195                 200                 205

Lys Lys Thr Gly His Asp Val Asp Phe Leu Ile Thr Ser Pro Gly Ser
    210                 215                 220

Thr Glu Glu Lys Glu Glu Glu Leu Leu Gln Lys Val Leu Asn Leu Trp
225                 230                 235                 240
```

-continued

```
Glu Lys Lys Gly Leu Leu Leu Tyr Tyr Asp Leu Val Glu Ser Thr Phe
             245             250             255

Glu Lys Leu Lys Thr Pro Ser Arg Lys Val Asp Ala Leu Asp His Phe
             260             265             270

Pro Lys Cys Phe Leu Ile Leu Lys Leu His His Gln Arg Val Asp Gly
             275             280             285

Asp Lys Pro Ser Gln Gln Glu Gly Lys Ser Trp Lys Ala Ile Arg Val
         290             295             300

Asp Leu Val Met Cys Pro Tyr Glu Arg His Ala Phe Ala Leu Leu Gly
305             310             315             320

Trp Thr Gly Ser Arg Gln Phe Glu Arg Asp Leu Arg Arg Tyr Ala Thr
             325             330             335

His Glu Arg Lys Met Met Leu Asp Asn His Ala Leu Tyr Asp Lys Thr
             340             345             350

Lys Arg Val Phe Leu Lys Ala Glu Ser Glu Glu Asp Ile Phe Ala His
             355             360             365

Leu Gly Leu Asp Tyr Ile Glu Pro Trp Glu Arg Asn Ala
         370             375             380
```

```
<210> SEQ ID NO 14
<211> LENGTH: 394
<212> TYPE: PRT
<213> ORGANISM: PLATYPUS

<400> SEQUENCE: 14
```

```
Leu Thr Asn Ser Ala Pro Ile Asn Cys Met Thr Glu Thr Pro Ser Leu
1               5               10              15

Ala Thr Lys Gln Val Ser Gln Tyr Ala Cys Glu Arg Arg Thr Thr Leu
             20              25              30

Asn Asn Cys Asn Gln Lys Phe Thr Asp Ala Phe Glu Ile Leu Ala Lys
         35              40              45

Asp Phe Glu Phe Arg Glu Asn Glu Gly Ile Cys Leu Ala Phe Met Arg
     50              55              60

Ala Ile Ser Val Leu Lys Cys Leu Pro Phe Thr Ile Val Arg Met Lys
65              70              75              80

Asp Ile Glu Gly Val Pro Trp Leu Gly Asp Gln Val Lys Ser Ile Ile
             85              90              95

Glu Glu Ile Ile Glu Asp Gly Glu Ser Ser Ser Val Lys Ala Val Leu
             100             105             110

Asn Asp Glu Arg Tyr Arg Ser Phe Gln Leu Phe Asn Ser Val Phe Glu
         115             120             125

Val Gly Leu Thr Asp Asn Gly Glu Asn Gly Ile Ala Arg Gly Phe Gln
     130             135             140

Thr Leu Asn Glu Val Ile Thr Asp Glu Asn Ile Ser Leu Thr Lys Thr
145             150             155             160

Thr Leu Ser Thr Ser Leu Trp Asn Tyr Leu Pro Gly Phe Leu Tyr Tyr
             165             170             175

Glu Asp Leu Val Ser Cys Val Ala Lys Glu Glu Ala Asp Ala Val Tyr
             180             185             190

Leu Ile Val Lys Glu Ala Val Arg Ala Phe Leu Pro Glu Ala Leu Val
         195             200             205

Thr Leu Thr Gly Gly Phe Arg Arg Gly Lys Lys Ile Gly His Asp Val
     210             215             220

Asp Phe Leu Ile Ser Asp Pro Glu Ser Gly Gln Asp Glu Gln Leu Leu
```

-continued

```
225                 230                 235                 240

Pro Asn Ile Ile Lys Leu Trp Glu Lys Gln Glu Leu Leu Tyr Tyr
                245                 250                 255

Asp Leu Val Glu Ser Thr Phe Glu Lys Thr Lys Ile Pro Ser Arg Lys
                260                 265                 270

Val Asp Ala Met Asp His Phe Gln Lys Cys Phe Leu Ile Leu Lys Leu
                275                 280                 285

His His Gln Lys Val Asp Ser Gly Arg Tyr Lys Pro Pro Pro Glu Ser
                290                 295                 300

Lys Asn His Glu Ala Lys Asn Trp Lys Ala Ile Arg Val Asp Leu Val
305                 310                 315                 320

Met Cys Pro Phe Glu Gln Tyr Ala Tyr Ala Leu Leu Gly Trp Thr Gly
                325                 330                 335

Ser Arg Gln Phe Glu Arg Asp Leu Arg Arg Tyr Ala Thr His Glu Lys
                340                 345                 350

Lys Met Met Leu Asp Asn His Ala Leu Tyr Asp Lys Thr Lys Lys Ile
                355                 360                 365

Phe Leu Lys Ala Glu Ser Glu Glu Asp Ile Phe Thr His Leu Gly Leu
                370                 375                 380

Asp Tyr Ile Glu Pro Trp Glu Arg Asn Ala
385                 390

<210> SEQ ID NO 15
<211> LENGTH: 384
<212> TYPE: PRT
<213> ORGANISM: JERBOA

<400> SEQUENCE: 15

Ser Ser Glu Leu Glu Leu Leu Asp Val Ser Trp Leu Ile Glu Cys Met
1               5                   10                  15

Gly Ala Gly Lys Pro Val Glu Met Thr Gly Arg His Gln Leu Val Lys
                20                  25                  30

Gln Thr Phe Cys Leu Pro Gly Phe Ile Leu Gln Asp Ala Phe Asp Ile
                35                  40                  45

Leu Ala Glu Asn Cys Glu Phe Arg Glu Asn Glu Ala Ser Cys Val Glu
                50                  55                  60

Phe Met Arg Ala Ala Ser Val Leu Lys Ser Leu Pro Phe Pro Ile Ile
65                  70                  75                  80

Ser Val Lys Asp Thr Glu Gly Ile Pro Trp Leu Gly Gly Lys Val Lys
                85                  90                  95

Cys Val Ile Glu Glu Ile Ile Glu Asp Gly Glu Ser Ser Glu Val Lys
                100                 105                 110

Ala Leu Leu Asn Asp Glu Arg Tyr Lys Ser Phe Lys Leu Phe Thr Ser
                115                 120                 125

Val Phe Gly Val Gly Leu Lys Thr Ala Glu Arg Trp Phe Arg Met Gly
                130                 135                 140

Phe Arg Thr Leu Ser Thr Val Lys Leu Asp Lys Ser Leu Thr Phe Thr
145                 150                 155                 160

Arg Met Gln Lys Ala Gly Phe Leu His Tyr Glu Asp Leu Val Ser Cys
                165                 170                 175

Val Thr Arg Ala Glu Ala Glu Ala Val Ser Val Leu Val Gln Gln Ala
                180                 185                 190

Val Val Ala Phe Leu Pro Asp Ala Leu Val Ser Met Thr Gly Gly Phe
                195                 200                 205
```

```
Arg Arg Gly Lys Lys Ile Gly His Asp Val Asp Phe Leu Ile Thr Ser
    210             215                 220

Pro Glu Ala Thr Glu Glu Glu Glu Gln Gln Leu Leu His Lys Val Thr
225             230                 235                 240

Asn Phe Trp Glu Gln Lys Gly Leu Leu Leu Tyr Cys Asp His Val Glu
                245                 250                 255

Ser Thr Phe Glu Lys Cys Lys Leu Pro Ser Arg Lys Val Asp Ala Leu
                260                 265                 270

Asp His Phe Gln Lys Cys Phe Leu Ile Leu Lys Leu Tyr Arg Glu Arg
            275                 280                 285

Val Asp Ser Val Lys Ser Ser Gln Gln Glu Gly Lys Gly Trp Lys Ala
    290                 295                 300

Ile Arg Val Asp Leu Val Met Cys Pro Tyr Glu Cys Arg Ala Phe Ala
305                 310                 315                 320

Leu Leu Gly Trp Thr Gly Ser Arg Gln Phe Glu Arg Asp Leu Arg Arg
                325                 330                 335

Tyr Ala Thr His Glu Arg Lys Met Arg Leu Asp Asn His Ala Leu Tyr
                340                 345                 350

Asp Lys Thr Lys Arg Val Phe Leu Lys Ala Glu Ser Glu Glu Glu Ile
            355                 360                 365

Phe Ala His Leu Gly Leu Glu Tyr Ile Glu Pro Leu Glu Arg Asn Ala
    370                 375                 380
```

```
<210> SEQ ID NO 16
<211> LENGTH: 362
<212> TYPE: PRT
<213> ORGANISM: Truncated mouse

<400> SEQUENCE: 16

Lys Ile Ser Gln Tyr Ala Cys Gln Arg Arg Thr Thr Leu Asn Asn Tyr
1               5                   10                  15

Asn Glu Leu Phe Thr Arg Ala Leu Asp Ile Leu Ala Glu Asn Asp Glu
                20                  25                  30

Phe Arg Glu Asn Glu Glu Ser Arg Asp Ala Phe Arg Arg Ala Ser Ser
            35                  40                  45

Val Leu Lys Ser Leu Pro Phe Pro Ile Thr Ser Met Lys Asp Thr Glu
    50                  55                  60

Gly Ile Pro Cys Leu Gly Asp Lys Val Lys Arg Ile Ile Glu Glu Ile
65                  70                  75                  80

Ile Glu Asp Gly Glu Ser Ser Glu Val Lys Ala Val Leu Asn Asp Glu
                85                  90                  95

Arg Tyr Lys Ala Phe Lys Leu Phe Thr Ser Val Phe Gly Val Gly Arg
                100                 105                 110

Lys Thr Ala Glu Lys Trp Phe Arg Met Gly Phe Arg Thr Leu Glu Lys
            115                 120                 125

Ile Arg Ser Asp Lys Ser Leu Arg Phe Thr Gln Met Gln Lys Ala Gly
    130                 135                 140

Phe Leu Tyr Tyr Glu Asp Leu Ala Glu Arg Val Asn Arg Pro Glu Ala
145                 150                 155                 160

Glu Ala Ile Arg Met Leu Val Lys Glu Ala Val Val Thr Phe Leu Pro
                165                 170                 175

Asp Ala Leu Val Thr Met Thr Gly Gly Phe Arg Leu Gly Lys Met Thr
                180                 185                 190

Gly His Asp Val Asp Phe Leu Ile Thr Ser Pro Glu Ala Thr Glu Asp
            195                 200                 205
```

-continued

```
Glu Glu Gln Gln Leu Leu His Lys Val Thr Asp Phe Trp Lys Gln Gln
    210             215             220

Gly Leu Leu Leu Tyr Cys Asp Ile Leu Glu Ser Thr Phe Glu Lys Phe
225             230             235             240

Lys Gln Pro Ser Arg Thr Val Asp Ala Leu Asp His Phe Gln Lys Cys
                245             250             255

Phe Leu Ile Leu Lys Leu Asp His Pro Arg Val His Ser Val Lys Ser
                260             265             270

Gly Gln Gln Glu Gly Lys Gly Trp Lys Ala Ile Arg Val Asp Leu Val
                275             280             285

Met Cys Pro Tyr Asp Arg Arg Ala Phe Ala Leu Leu Gly Trp Thr Gly
    290             295             300

Ser Pro Gln Phe Asn Arg Asp Leu Arg Arg Tyr Ala Thr His Glu Arg
305             310             315             320

Lys Met Met Leu Asp Asn His Ala Leu Tyr Asp Lys Thr Lys Arg Val
                325             330             335

Phe Leu Glu Ala Glu Ser Glu Glu Glu Ile Phe Ala His Leu Gly Leu
                340             345             350

Asp Tyr Ile Glu Pro Trp Glu Arg Asn Ala
        355             360
```

```
<210> SEQ ID NO 17
<211> LENGTH: 361
<212> TYPE: PRT
<213> ORGANISM: Artificial Sequence
<220> FEATURE:
<223> OTHER INFORMATION: bovine-mouse chimera (M57 without His tag &
      linker)

<400> SEQUENCE: 17
```

```
Lys Ile Ser Gln Tyr Ala Cys Gln Arg Arg Thr Thr Leu Asn Asn Tyr
1               5               10              15

Asn Glu Leu Phe Thr Arg Ala Leu Asp Ile Leu Ala Glu Asn Asp Glu
                20              25              30

Phe Arg Glu Asn Glu Glu Ser Arg Asp Ala Phe Arg Arg Ala Ser Ser
        35              40              45

Val Leu Lys Ser Leu Pro Phe Pro Ile Thr Ser Met Lys Asp Thr Glu
    50              55              60

Gly Ile Pro Cys Leu Gly Asp Lys Val Lys Arg Ile Ile Glu Glu Ile
65              70              75              80

Ile Glu Asp Gly Glu Ser Ser Glu Val Lys Ala Val Leu Asn Asp Glu
                85              90              95

Arg Tyr Lys Ala Phe Lys Leu Phe Thr Ser Val Phe Gly Val Gly Arg
            100             105             110

Lys Thr Ala Glu Lys Trp Phe Arg Met Gly Phe Arg Thr Leu Glu Lys
        115             120             125

Ile Arg Ser Asp Lys Ser Leu Arg Phe Thr Gln Met Gln Lys Ala Gly
    130             135             140

Phe Leu Tyr Tyr Glu Asp Leu Val Ser Gly Val Thr Arg Ala Glu Ala
145             150             155             160

Glu Ala Val Gly Val Leu Val Lys Glu Ala Val Trp Ala Phe Leu Pro
            165             170             175

Asp Ala Phe Val Thr Met Thr Gly Gly Phe Arg Leu Gly Lys Lys Ile
            180             185             190

Gly His Asp Val Asp Phe Leu Ile Thr Ser Pro Gly Ser Ala Glu Asp
```

-continued

```
            195                 200                 205
Glu Glu Gln Leu Leu Pro Lys Val Ile Asn Leu Trp Glu Lys Lys Gly
    210                 215                 220

Leu Leu Leu Tyr Tyr Asp Leu Val Glu Ser Thr Phe Glu Lys Phe Lys
225                 230                 235                 240

Leu Pro Ser Arg Gln Val Asp Thr Leu Asp His Phe Gln Lys Cys Phe
                245                 250                 255

Leu Ile Leu Lys Leu His His Gln Arg Val Asp Ser Ser Lys Ser Asn
                260                 265                 270

Gln Gln Glu Gly Lys Thr Trp Lys Ala Ile Arg Val Asp Leu Val Met
                275                 280                 285

Cys Pro Tyr Glu Asn Arg Ala Phe Ala Leu Leu Gly Trp Thr Gly Ser
    290                 295                 300

Pro Gln Phe Asn Arg Asp Leu Arg Arg Tyr Ala Thr His Glu Arg Lys
305                 310                 315                 320

Met Met Leu Asp Asn His Ala Leu Tyr Asp Lys Thr Lys Arg Val Phe
                325                 330                 335

Leu Glu Ala Glu Ser Glu Glu Glu Ile Phe Ala His Leu Gly Leu Asp
                340                 345                 350

Tyr Ile Glu Pro Trp Glu Arg Asn Ala
                355                 360
```

```
<210> SEQ ID NO 18
<211> LENGTH: 361
<212> TYPE: PRT
<213> ORGANISM: Artificial Sequence
<220> FEATURE:
<223> OTHER INFORMATION: bovine-mouse chimera (M59 without His Tag and
      linker)

<400> SEQUENCE: 18
```

```
Lys Ile Ser Gln Tyr Ala Cys Gln Arg Arg Thr Thr Leu Asn Asn Tyr
1               5                   10                  15

Asn Glu Leu Phe Thr Arg Ala Leu Asp Ile Leu Ala Glu Asn Asp Glu
                20                  25                  30

Phe Arg Glu Asn Glu Glu Ser Arg Asp Ala Phe Arg Arg Ala Ser Ser
        35                  40                  45

Val Leu Lys Ser Leu Pro Phe Pro Ile Thr Ser Met Lys Asp Thr Glu
    50                  55                  60

Gly Ile Pro Cys Leu Gly Asp Lys Val Lys Arg Ile Ile Glu Glu Ile
65                  70                  75                  80

Ile Glu Asp Gly Glu Ser Ser Glu Val Lys Ala Val Leu Asn Asp Glu
                85                  90                  95

Arg Tyr Lys Ala Phe Lys Leu Phe Thr Ser Val Phe Gly Val Gly Arg
            100                 105                 110

Lys Thr Ala Glu Lys Trp Phe Arg Met Gly Phe Arg Thr Leu Glu Lys
        115                 120                 125

Ile Arg Ser Asp Lys Ser Leu Arg Phe Thr Gln Met Gln Lys Ala Gly
    130                 135                 140

Phe Leu Tyr Tyr Glu Asp Leu Ala Glu Arg Val Asn Arg Pro Glu Ala
145                 150                 155                 160

Glu Ala Ile Arg Met Leu Val Lys Glu Ala Val Val Thr Phe Leu Pro
                165                 170                 175

Asp Ala Leu Val Thr Met Thr Gly Gly Phe Arg Leu Gly Lys Met Thr
                180                 185                 190
```

-continued

```
Gly His Asp Val Asp Phe Leu Ile Thr Ser Pro Gly Ser Ala Glu Asp
        195                 200                 205

Glu Glu Gln Leu Leu Pro Lys Val Ile Asn Leu Trp Glu Lys Lys Gly
    210                 215                 220

Leu Leu Leu Tyr Tyr Asp Leu Val Glu Ser Thr Phe Glu Lys Phe Lys
225                 230                 235                 240

Leu Pro Ser Arg Gln Val Asp Thr Leu Asp His Phe Gln Lys Cys Phe
                245                 250                 255

Leu Ile Leu Lys Leu His His Gln Arg Val Asp Ser Ser Lys Ser Asn
            260                 265                 270

Gln Gln Glu Gly Lys Thr Trp Lys Ala Ile Arg Val Asp Leu Val Met
        275                 280                 285

Cys Pro Tyr Glu Asn Arg Ala Phe Ala Leu Leu Gly Trp Thr Gly Ser
    290                 295                 300

Pro Gln Phe Asn Arg Asp Leu Arg Arg Tyr Ala Thr His Glu Arg Lys
305                 310                 315                 320

Met Met Leu Asp Asn His Ala Leu Tyr Asp Lys Thr Lys Arg Val Phe
                325                 330                 335

Leu Glu Ala Glu Ser Glu Glu Ile Phe Ala His Leu Gly Leu Asp
            340                 345                 350

Tyr Ile Glu Pro Trp Glu Arg Asn Ala
        355                 360

<210> SEQ ID NO 19
<211> LENGTH: 361
<212> TYPE: PRT
<213> ORGANISM: mouse

<400> SEQUENCE: 19

Lys Ile Ser Gln Tyr Ala Cys Gln Arg Arg Thr Thr Leu Asn Asn Tyr
1               5                   10                  15

Asn Glu Leu Phe Thr Arg Ala Leu Asp Ile Leu Ala Glu Asn Asp Glu
                20                  25                  30

Phe Arg Glu Asn Glu Glu Ser Arg Asp Ala Phe Arg Arg Ala Ser Ser
            35                  40                  45

Val Leu Lys Ser Leu Pro Phe Pro Ile Thr Ser Met Lys Asp Thr Glu
    50                  55                  60

Gly Ile Pro Cys Leu Gly Asp Lys Val Lys Arg Ile Ile Glu Glu Ile
65                  70                  75                  80

Ile Glu Asp Gly Glu Ser Ser Glu Val Lys Ala Val Leu Asn Asp Glu
                85                  90                  95

Arg Tyr Lys Ala Phe Lys Leu Phe Thr Ser Val Phe Gly Val Gly Arg
            100                 105                 110

Lys Thr Ala Glu Lys Trp Phe Arg Met Gly Phe Arg Thr Leu Glu Lys
        115                 120                 125

Ile Arg Ser Asp Lys Ser Leu Arg Phe Thr Gln Met Gln Lys Ala Gly
    130                 135                 140

Phe Leu Tyr Tyr Glu Asp Leu Ala Glu Arg Val Asn Arg Pro Glu Ala
145                 150                 155                 160

Glu Ala Ile Arg Met Leu Val Lys Glu Ala Val Val Thr Phe Leu Pro
                165                 170                 175

Asp Ala Leu Val Thr Met Thr Gly Gly Phe Arg Leu Gly Lys Met Thr
            180                 185                 190

Gly His Asp Val Asp Phe Leu Ile Thr Ser Pro Gly Ser Ala Glu Asp
        195                 200                 205
```

-continued

```
Glu Glu Gln Leu Leu Pro Lys Val Ile Asn Leu Trp Glu Lys Lys Gly
    210                 215                 220

Leu Leu Leu Tyr Tyr Asp Leu Val Glu Ser Thr Phe Glu Lys Phe Lys
225                 230                 235                 240

Leu Pro Ser Arg Gln Val Asp Thr Leu Asp His Phe Gln Lys Cys Phe
                245                 250                 255

Leu Ile Leu Lys Leu His His Gln Arg Val Asp Ser Ser Lys Ser Asn
                260                 265                 270

Gln Gln Glu Gly Lys Thr Trp Lys Ala Ile Arg Val Asp Leu Val Met
                275                 280                 285

Cys Pro Tyr Glu Asn Arg Ala Phe Ala Leu Leu Gly Trp Thr Gly Ser
    290                 295                 300

Pro Gln Phe Asn Arg Asp Leu Arg Arg Tyr Ala Thr His Glu Arg Lys
305                 310                 315                 320

Met Met Leu Asp Asn His Ala Leu Tyr Asp Lys Thr Lys Arg Val Phe
                325                 330                 335

Leu Glu Ala Glu Ser Glu Glu Glu Ile Phe Ala His Leu Gly Leu Asp
                340                 345                 350

Tyr Ile Glu Pro Trp Glu Arg Asn Ala
        355                 360

<210> SEQ ID NO 20
<211> LENGTH: 361
<212> TYPE: PRT
<213> ORGANISM: Artificial Sequence
<220> FEATURE:
<223> OTHER INFORMATION: M54

<400> SEQUENCE: 20

Lys Ile Ser Gln Tyr Ala Cys Gln Arg Lys Thr Thr Leu Asn Asn Tyr
1               5                   10                  15

Asn Glu Ile Phe Thr Arg Ala Phe Glu Ile Leu Ala Glu Asn Ser Glu
            20                  25                  30

Phe Lys Glu Asn Glu Glu Ser Tyr Val Thr Phe Arg Arg Ala Ala Ser
        35                  40                  45

Val Leu Lys Ser Leu Pro Phe Thr Ile Ile Ser Met Lys Asp Thr Glu
    50                  55                  60

Gly Ile Pro Cys Leu Gly Asp Lys Val Lys Arg Ile Ile Glu Glu Ile
65                  70                  75                  80

Ile Glu Asp Gly Glu Ser Ser Glu Val Lys Ala Val Leu Asn Asp Glu
                85                  90                  95

Arg Tyr Gln Ala Phe Lys Leu Phe Thr Ser Val Phe Gly Val Gly Arg
            100                 105                 110

Lys Thr Ser Glu Lys Trp Phe Arg Met Gly Phe Arg Ser Leu Glu Lys
            115                 120                 125

Ile Arg Ser Asp Lys Thr Leu Lys Phe Thr Lys Met Gln Lys Ala Gly
    130                 135                 140

Phe Leu Tyr Tyr Glu Asp Leu Val Ser Gly Val Thr Arg Ala Glu Ala
145                 150                 155                 160

Glu Ala Val Gly Val Leu Val Lys Glu Ala Val Trp Ala Phe Leu Pro
                165                 170                 175

Asp Ala Phe Val Thr Met Thr Gly Gly Phe Arg Leu Gly Lys Lys Ile
            180                 185                 190

Gly His Asp Val Asp Phe Leu Ile Thr Ser Pro Gly Ser Ala Glu Asp
        195                 200                 205
```

-continued

```
Glu Glu Gln Leu Leu Pro Lys Val Ile Asn Leu Trp Glu Lys Lys Gly
    210             215             220

Leu Leu Leu Tyr Tyr Asp Leu Val Glu Ser Thr Phe Glu Lys Phe Lys
225             230             235             240

Leu Pro Ser Arg Gln Val Asp Thr Leu Asp His Phe Gln Lys Cys Phe
            245             250             255

Leu Ile Leu Lys Leu His His Gln Arg Val Asp Ser Ser Lys Ser Asn
            260             265             270

Gln Gln Glu Gly Lys Thr Trp Lys Ala Ile Arg Val Asp Leu Val Met
            275             280             285

Cys Pro Tyr Glu Asn Arg Ala Phe Ala Leu Leu Gly Trp Thr Gly Ser
    290             295             300

Ala Phe Phe Asn Arg Asp Ile Arg Arg Tyr Ala Thr His Glu Arg Lys
305             310             315             320

Met Met Leu Asp Asn His Ala Leu Tyr Asp Lys Thr Lys Arg Val Phe
            325             330             335

Leu Lys Ala Glu Ser Glu Glu Glu Ile Phe Ala His Leu Gly Leu Asp
            340             345             350

Tyr Ile Glu Pro Arg Glu Arg Asn Ala
    355             360
```

<210> SEQ ID NO 21
<211> LENGTH: 362
<212> TYPE: PRT
<213> ORGANISM: Artificial Sequence
<220> FEATURE:
<223> OTHER INFORMATION: M77 without His tag

<400> SEQUENCE: 21

```
Lys Lys Ile Ser Glu Tyr Ala Cys Gln Arg Arg Thr Thr Leu Asn Asn
1               5               10              15

Tyr Asn Glu Leu Phe Thr Arg Ala Leu Asp Ile Leu Ala Glu Asn Asp
            20              25              30

Glu Phe Arg Glu Asn Glu Glu Ser Arg Asp Ala Phe Arg Arg Ala Ser
        35              40              45

Ser Val Leu Lys Ser Leu Pro Phe Pro Ile Thr Ser Met Lys Asp Thr
    50              55              60

Glu Gly Ile Pro Cys Leu Gly Asp Lys Val Lys Arg Ile Ile Glu Glu
65              70              75              80

Ile Ile Glu Asp Gly Glu Ser Ser Glu Val Lys Ala Val Leu Asn Asp
            85              90              95

Glu Arg Tyr Lys Ala Phe Lys Leu Phe Thr Ser Val Phe Gly Val Gly
            100             105             110

Arg Lys Thr Ala Glu Lys Trp Phe Arg Met Gly Phe Arg Thr Leu Glu
            115             120             125

Lys Ile Arg Ser Asp Lys Ser Leu Arg Phe Thr Gln Met Gln Lys Ala
    130             135             140

Gly Phe Leu Tyr Tyr Glu Asp Leu Val Ser Gly Val Thr Arg Ala Glu
145             150             155             160

Ala Glu Ala Val Gly Val Leu Val Lys Glu Ala Val Trp Ala Phe Leu
            165             170             175

Pro Asp Ala Phe Val Thr Met Thr Gly Gly Phe Arg Leu Gly Lys Lys
            180             185             190

Ile Gly His Asp Val Asp Phe Leu Ile Thr Ser Pro Gly Ser Ala Glu
            195             200             205
```

```
Asp Glu Glu Gln Leu Leu Pro Lys Val Ile Asn Leu Trp Glu Lys Lys
    210             215             220

Gly Leu Leu Leu Tyr Tyr Asp Leu Val Glu Ser Thr Phe Glu Lys Phe
225             230             235             240

Lys Leu Pro Ser Arg Gln Val Asp Thr Leu Asp His Phe Gln Lys Cys
            245             250             255

Phe Leu Ile Leu Lys Leu His His Gln Arg Val Asp Ser Ser Lys Ser
            260             265             270

Asn Gln Gln Glu Gly Lys Thr Trp Lys Ala Ile Arg Val Asp Leu Val
    275             280             285

Met Cys Pro Tyr Glu Asn Arg Ala Phe Ala Leu Leu Gly Trp Thr Gly
    290             295             300

Ser Pro Gln Phe Asn Arg Asp Leu Arg Arg Tyr Ala Thr His Glu Arg
305             310             315             320

Lys Met Met Leu Asp Asn His Ala Leu Tyr Asp Lys Thr Lys Arg Val
            325             330             335

Phe Leu Glu Ala Glu Ser Glu Glu Glu Ile Phe Ala His Leu Gly Leu
            340             345             350

Asp Tyr Ile Glu Pro Trp Glu Arg Asn Ala
        355             360
```

```
<210> SEQ ID NO 22
<211> LENGTH: 377
<212> TYPE: PRT
<213> ORGANISM: Artificial Sequence
<220> FEATURE:
<223> OTHER INFORMATION: M77 with His tag

<400> SEQUENCE: 22

Met Ala Ser Ser His His His His His His Ser Ser Gly Ser Glu Lys
1               5               10              15

Lys Ile Ser Glu Tyr Ala Cys Gln Arg Arg Thr Thr Leu Asn Asn Tyr
        20              25              30

Asn Glu Leu Phe Thr Arg Ala Leu Asp Ile Leu Ala Glu Asn Asp Glu
        35              40              45

Phe Arg Glu Asn Glu Glu Ser Arg Asp Ala Phe Arg Arg Ala Ser Ser
    50              55              60

Val Leu Lys Ser Leu Pro Phe Pro Ile Thr Ser Met Lys Asp Thr Glu
65              70              75              80

Gly Ile Pro Cys Leu Gly Asp Lys Val Lys Arg Ile Ile Glu Glu Ile
            85              90              95

Ile Glu Asp Gly Glu Ser Ser Glu Val Lys Ala Val Leu Asn Asp Glu
            100             105             110

Arg Tyr Lys Ala Phe Lys Leu Phe Thr Ser Val Phe Gly Val Gly Arg
            115             120             125

Lys Thr Ala Glu Lys Trp Phe Arg Met Gly Phe Arg Thr Leu Glu Lys
    130             135             140

Ile Arg Ser Asp Lys Ser Leu Arg Phe Thr Gln Met Gln Lys Ala Gly
145             150             155             160

Phe Leu Tyr Tyr Glu Asp Leu Val Ser Gly Val Thr Arg Ala Glu Ala
            165             170             175

Glu Ala Val Gly Val Leu Val Lys Glu Ala Val Trp Ala Phe Leu Pro
            180             185             190

Asp Ala Phe Val Thr Met Thr Gly Gly Phe Arg Leu Gly Lys Lys Ile
            195             200             205
```

```
Gly His Asp Val Asp Phe Leu Ile Thr Ser Pro Gly Ser Ala Glu Asp
    210                 215                 220

Glu Glu Gln Leu Leu Pro Lys Val Ile Asn Leu Trp Glu Lys Lys Gly
225                 230                 235                 240

Leu Leu Leu Tyr Tyr Asp Leu Val Glu Ser Thr Phe Glu Lys Phe Lys
                245                 250                 255

Leu Pro Ser Arg Gln Val Asp Thr Leu Asp His Phe Gln Lys Cys Phe
                260                 265                 270

Leu Ile Leu Lys Leu His His Gln Arg Val Asp Ser Ser Lys Ser Asn
            275                 280                 285

Gln Gln Glu Gly Lys Thr Trp Lys Ala Ile Arg Val Asp Leu Val Met
    290                 295                 300

Cys Pro Tyr Glu Asn Arg Ala Phe Ala Leu Leu Gly Trp Thr Gly Ser
305                 310                 315                 320

Pro Gln Phe Asn Arg Asp Leu Arg Arg Tyr Ala Thr His Glu Arg Lys
                325                 330                 335

Met Met Leu Asp Asn His Ala Leu Tyr Asp Lys Thr Lys Arg Val Phe
                340                 345                 350

Leu Glu Ala Glu Ser Glu Glu Glu Ile Phe Ala His Leu Gly Leu Asp
            355                 360                 365

Tyr Ile Glu Pro Trp Glu Arg Asn Ala
    370                 375
```

```
<210> SEQ ID NO 23
<211> LENGTH: 361
<212> TYPE: PRT
<213> ORGANISM: Artificial Sequence
<220> FEATURE:
<223> OTHER INFORMATION: C1-40 without His tag

<400> SEQUENCE: 23

Lys Ile Ser Glu Tyr Ala Cys Gln Arg Arg Thr Thr Leu Asn Asn Tyr
1               5                   10                  15

Asn Glu Leu Phe Thr Arg Ala Leu Asp Ile Leu Ala Glu Asn Asp Glu
                20                  25                  30

Phe Arg Glu Asn Glu Glu Ser Arg Asp Ala Phe Arg Arg Ala Ser Ser
            35                  40                  45

Val Leu Lys Ser Leu Pro Phe Pro Ile Thr Ser Met Lys Asp Thr Glu
    50                  55                  60

Gly Ile Pro Cys Leu Gly Asp Lys Val Lys Arg Ile Ile Glu Glu Ile
65                  70                  75                  80

Ile Glu Asp Gly Glu Ser Ser Glu Val Lys Ala Val Leu Asn Asp Glu
                85                  90                  95

Arg Tyr Lys Ala Phe Lys Leu Phe Thr Ser Val Phe Gly Val Gly Arg
                100                 105                 110

Lys Thr Ala Glu Lys Trp Phe Arg Met Gly Phe Arg Thr Leu Glu Lys
            115                 120                 125

Ile Arg Ser Asp Lys Ser Leu Arg Phe Thr Gln Met Gln Lys Ala Gly
    130                 135                 140

Phe Leu Tyr Tyr Glu Asp Leu Val Ser Gly Val Thr Arg Ala Glu Ala
145                 150                 155                 160

Glu Ala Val Gly Val Leu Val Lys Glu Ala Val Trp Ala Phe Leu Pro
                165                 170                 175

Asp Ala Phe Val Thr Met Thr Gly Gly Phe Arg Leu Gly Lys Lys Ile
                180                 185                 190
```

-continued

```
Gly His Asp Val Asp Phe Leu Ile Thr Ser Pro Gly Ser Ala Glu Asp
        195                 200                 205

Glu Glu Gln Leu Leu Pro Lys Val Ile Asn Leu Trp Glu Lys Lys Gly
        210                 215                 220

Leu Leu Leu Tyr Tyr Asp Leu Val Glu Ser Thr Phe Glu Lys Phe Lys
225                 230                 235                 240

Leu Pro Ser Arg Gln Val Asp Thr Leu Asp His Phe Gln Lys Cys Phe
                245                 250                 255

Leu Ile Leu Lys Leu His His Gln Arg Val Asp Ser Ser Lys Ser Asn
                260                 265                 270

Gln Gln Glu Gly Lys Thr Trp Lys Ala Ile Arg Val Asp Leu Val Met
                275                 280                 285

Cys Pro Tyr Glu Asn Arg Ala Phe Ala Leu Leu Gly Trp Thr Gly Ser
        290                 295                 300

Pro Gln Phe Asn Arg Asp Leu Arg Arg Tyr Ala Thr His Glu Arg Lys
305                 310                 315                 320

Met Met Leu Asp Asn His Ala Leu Tyr Asp Lys Thr Lys Arg Val Phe
                325                 330                 335

Leu Glu Ala Glu Ser Glu Glu Glu Ile Phe Ala His Leu Gly Leu Asp
                340                 345                 350

Tyr Ile Glu Pro Trp Glu Arg Asn Ala
        355                 360

<210> SEQ ID NO 24
<211> LENGTH: 376
<212> TYPE: PRT
<213> ORGANISM: Artificial Sequence
<220> FEATURE:
<223> OTHER INFORMATION: C1-40 with His tag

<400> SEQUENCE: 24

Met Ala Ser Ser His His His His His His Ser Ser Gly Ser Glu Lys
1               5                   10                  15

Ile Ser Glu Tyr Ala Cys Gln Arg Arg Thr Thr Leu Asn Asn Tyr Asn
                20                  25                  30

Glu Leu Phe Thr Arg Ala Leu Asp Ile Leu Ala Glu Asn Asp Glu Phe
        35                  40                  45

Arg Glu Asn Glu Glu Ser Arg Asp Ala Phe Arg Arg Ala Ser Ser Val
        50                  55                  60

Leu Lys Ser Leu Pro Phe Pro Ile Thr Ser Met Lys Asp Thr Glu Gly
65                  70                  75                  80

Ile Pro Cys Leu Gly Asp Lys Val Lys Arg Ile Ile Glu Glu Ile Ile
                85                  90                  95

Glu Asp Gly Glu Ser Ser Glu Val Lys Ala Val Leu Asn Asp Glu Arg
                100                 105                 110

Tyr Lys Ala Phe Lys Leu Phe Thr Ser Val Phe Gly Val Gly Arg Lys
        115                 120                 125

Thr Ala Glu Lys Trp Phe Arg Met Gly Phe Arg Thr Leu Glu Lys Ile
        130                 135                 140

Arg Ser Asp Lys Ser Leu Arg Phe Thr Gln Met Gln Lys Ala Gly Phe
145                 150                 155                 160

Leu Tyr Tyr Glu Asp Leu Val Ser Gly Val Thr Arg Ala Glu Ala Glu
                165                 170                 175

Ala Val Gly Val Leu Val Lys Glu Ala Val Trp Ala Phe Leu Pro Asp
                180                 185                 190
```

-continued

```
Ala Phe Val Thr Met Thr Gly Gly Phe Arg Leu Gly Lys Lys Ile Gly
        195                 200                 205

His Asp Val Asp Phe Leu Ile Thr Ser Pro Gly Ser Ala Glu Asp Glu
        210                 215                 220

Glu Gln Leu Leu Pro Lys Val Ile Asn Leu Trp Glu Lys Lys Gly Leu
225                 230                 235                 240

Leu Leu Tyr Tyr Asp Leu Val Glu Ser Thr Phe Glu Lys Phe Lys Leu
                245                 250                 255

Pro Ser Arg Gln Val Asp Thr Leu Asp His Phe Gln Lys Cys Phe Leu
                260                 265                 270

Ile Leu Lys Leu His His Gln Arg Val Asp Ser Ser Lys Ser Asn Gln
        275                 280                 285

Gln Glu Gly Lys Thr Trp Lys Ala Ile Arg Val Asp Leu Val Met Cys
        290                 295                 300

Pro Tyr Glu Asn Arg Ala Phe Ala Leu Leu Gly Trp Thr Gly Ser Pro
305                 310                 315                 320

Gln Phe Asn Arg Asp Leu Arg Arg Tyr Ala Thr His Glu Arg Lys Met
                325                 330                 335

Met Leu Asp Asn His Ala Leu Tyr Asp Lys Thr Lys Arg Val Phe Leu
        340                 345                 350

Glu Ala Glu Ser Glu Glu Glu Ile Phe Ala His Leu Gly Leu Asp Tyr
        355                 360                 365

Ile Glu Pro Trp Glu Arg Asn Ala
        370                 375
```

```
<210> SEQ ID NO 25
<211> LENGTH: 363
<212> TYPE: PRT
<213> ORGANISM: Artificial Sequence
<220> FEATURE:
<223> OTHER INFORMATION: A2-20 without His tag

<400> SEQUENCE: 25

Val Thr Thr Val Ser Glu Tyr Ala Cys Gln Arg Arg Thr Thr Leu Asn
1               5                   10                  15

Asn Tyr Asn Glu Leu Phe Thr Arg Ala Leu Asp Ile Leu Ala Glu Asn
                20                  25                  30

Asp Glu Phe Arg Glu Asn Glu Glu Ser Arg Asp Ala Phe Arg Arg Ala
        35                  40                  45

Ser Ser Val Leu Lys Ser Leu Pro Phe Pro Ile Thr Ser Met Lys Asp
        50                  55                  60

Thr Glu Gly Ile Pro Cys Leu Gly Asp Lys Val Lys Arg Ile Ile Glu
65                  70                  75                  80

Glu Ile Ile Glu Asp Gly Glu Ser Ser Glu Val Lys Ala Val Leu Asn
                85                  90                  95

Asp Glu Arg Tyr Lys Ala Phe Lys Leu Phe Thr Ser Val Phe Gly Val
                100                 105                 110

Gly Arg Lys Thr Ala Glu Lys Trp Phe Arg Met Gly Phe Arg Thr Leu
        115                 120                 125

Glu Lys Ile Arg Ser Asp Lys Ser Leu Arg Phe Thr Gln Met Gln Lys
        130                 135                 140

Ala Gly Phe Leu Tyr Tyr Glu Asp Leu Val Ser Gly Val Thr Arg Ala
145                 150                 155                 160

Glu Ala Glu Ala Val Gly Val Leu Val Lys Glu Ala Val Trp Ala Phe
                165                 170                 175
```

-continued

```
Leu Pro Asp Ala Phe Val Thr Met Thr Gly Gly Phe Arg Leu Gly Lys
        180                 185                 190

Lys Ile Gly His Asp Val Asp Phe Leu Ile Thr Ser Pro Gly Ser Ala
        195                 200                 205

Glu Asp Glu Glu Gln Leu Leu Pro Lys Val Ile Asn Leu Trp Glu Lys
    210                 215                 220

Lys Gly Leu Leu Leu Tyr Tyr Asp Leu Val Glu Ser Thr Phe Glu Lys
225                 230                 235                 240

Phe Lys Leu Pro Ser Arg Gln Val Asp Thr Leu Asp His Phe Gln Lys
                245                 250                 255

Cys Phe Leu Ile Leu Lys Leu His His Gln Arg Val Asp Ser Ser Lys
                260                 265                 270

Ser Asn Gln Gln Glu Gly Lys Thr Trp Lys Ala Ile Arg Val Asp Leu
        275                 280                 285

Val Met Cys Pro Tyr Glu Asn Arg Ala Phe Ala Leu Leu Gly Trp Thr
    290                 295                 300

Gly Ser Pro Gln Phe Asn Arg Asp Leu Arg Arg Tyr Ala Thr His Glu
305                 310                 315                 320

Arg Lys Met Met Leu Asp Asn His Ala Leu Tyr Asp Lys Thr Lys Arg
                325                 330                 335

Val Phe Leu Glu Ala Glu Ser Glu Glu Ile Phe Ala His Leu Gly
                340                 345                 350

Leu Asp Tyr Ile Glu Pro Trp Glu Arg Asn Ala
        355                 360
```

<210> SEQ ID NO 26
<211> LENGTH: 379
<212> TYPE: PRT
<213> ORGANISM: Artificial Sequence
<220> FEATURE:
<223> OTHER INFORMATION: A2-20 with His tag

<400> SEQUENCE: 26

```
Met Ala Ser Ser His His His His His His Ser Ser Gly Ser Glu Asn
1               5                   10                  15

Val Thr Thr Val Ser Glu Tyr Ala Cys Gln Arg Arg Thr Thr Leu Asn
            20                  25                  30

Asn Tyr Asn Glu Leu Phe Thr Arg Ala Leu Asp Ile Leu Ala Glu Asn
        35                  40                  45

Asp Glu Phe Arg Glu Asn Glu Glu Ser Arg Asp Ala Phe Arg Arg Ala
    50                  55                  60

Ser Ser Val Leu Lys Ser Leu Pro Phe Pro Ile Thr Ser Met Lys Asp
65                  70                  75                  80

Thr Glu Gly Ile Pro Cys Leu Gly Asp Lys Val Lys Arg Ile Ile Glu
                85                  90                  95

Glu Ile Ile Glu Asp Gly Glu Ser Ser Glu Val Lys Ala Val Leu Asn
            100                 105                 110

Asp Glu Arg Tyr Lys Ala Phe Lys Leu Phe Thr Ser Val Phe Gly Val
        115                 120                 125

Gly Arg Lys Thr Ala Glu Lys Trp Phe Arg Met Gly Phe Arg Thr Leu
    130                 135                 140

Glu Lys Ile Arg Ser Asp Lys Ser Leu Arg Phe Thr Gln Met Gln Lys
145                 150                 155                 160

Ala Gly Phe Leu Tyr Tyr Glu Asp Leu Val Ser Gly Val Thr Arg Ala
                165                 170                 175
```

-continued

```
Glu Ala Glu Ala Val Gly Val Leu Val Lys Glu Ala Val Trp Ala Phe
            180                 185                 190

Leu Pro Asp Ala Phe Val Thr Met Thr Gly Gly Phe Arg Leu Gly Lys
            195                 200                 205

Lys Ile Gly His Asp Val Asp Phe Leu Ile Thr Ser Pro Gly Ser Ala
            210                 215                 220

Glu Asp Glu Glu Gln Leu Leu Pro Lys Val Ile Asn Leu Trp Glu Lys
225                 230                 235                 240

Lys Gly Leu Leu Leu Tyr Tyr Asp Leu Val Glu Ser Thr Phe Glu Lys
                245                 250                 255

Phe Lys Leu Pro Ser Arg Gln Val Asp Thr Leu Asp His Phe Gln Lys
            260                 265                 270

Cys Phe Leu Ile Leu Lys Leu His His Gln Arg Val Asp Ser Ser Lys
            275                 280                 285

Ser Asn Gln Gln Glu Gly Lys Thr Trp Lys Ala Ile Arg Val Asp Leu
            290                 295                 300

Val Met Cys Pro Tyr Glu Asn Arg Ala Phe Ala Leu Leu Gly Trp Thr
305                 310                 315                 320

Gly Ser Pro Gln Phe Asn Arg Asp Leu Arg Arg Tyr Ala Thr His Glu
                325                 330                 335

Arg Lys Met Met Leu Asp Asn His Ala Leu Tyr Asp Lys Thr Lys Arg
                340                 345                 350

Val Phe Leu Glu Ala Glu Ser Glu Glu Glu Ile Phe Ala His Leu Gly
            355                 360                 365

Leu Asp Tyr Ile Glu Pro Trp Glu Arg Asn Ala
            370                 375

<210> SEQ ID NO 27
<211> LENGTH: 363
<212> TYPE: PRT
<213> ORGANISM: Artificial Sequence
<220> FEATURE:
<223> OTHER INFORMATION: ii-ell-40 without His tag

<400> SEQUENCE: 27

Val Ala Thr Val Ser Glu Tyr Ala Cys Gln Arg Arg Thr Thr Leu Asn
1               5                   10                  15

Asn Tyr Asn Glu Leu Phe Thr Arg Ala Leu Asp Ile Leu Ala Glu Asn
            20                  25                  30

Asp Glu Phe Arg Glu Asn Glu Glu Ser Arg Asp Ala Phe Arg Arg Ala
            35                  40                  45

Ser Ser Val Leu Lys Ser Leu Pro Phe Pro Ile Thr Ser Met Lys Asp
            50                  55                  60

Thr Glu Gly Ile Pro Cys Leu Gly Asp Lys Val Lys Arg Ile Ile Glu
65                  70                  75                  80

Glu Ile Ile Glu Asp Gly Glu Ser Ser Glu Val Lys Ala Val Leu Asn
                85                  90                  95

Asp Glu Arg Tyr Lys Ala Phe Lys Leu Phe Thr Ser Val Phe Gly Val
            100                 105                 110

Gly Arg Lys Thr Ala Glu Lys Trp Phe Arg Met Gly Phe Arg Thr Leu
            115                 120                 125

Glu Lys Ile Arg Ser Asp Lys Ser Leu Arg Phe Thr Gln Met Gln Lys
            130                 135                 140

Ala Gly Phe Leu Tyr Tyr Glu Asp Leu Val Ser Gly Val Thr Arg Ala
145                 150                 155                 160
```

-continued

```
Glu Ala Glu Ala Val Gly Val Leu Val Lys Glu Ala Val Trp Ala Phe
            165             170             175

Leu Pro Asp Ala Phe Val Thr Met Thr Gly Gly Phe Arg Leu Gly Lys
            180             185             190

Lys Ile Gly His Asp Val Asp Phe Leu Ile Thr Ser Pro Gly Ser Ala
            195             200             205

Glu Asp Glu Glu Gln Leu Leu Pro Lys Val Ile Asn Leu Trp Glu Lys
        210             215             220

Lys Gly Leu Leu Leu Tyr Tyr Asp Leu Val Glu Ser Thr Phe Glu Lys
    225             230             235             240

Phe Lys Leu Pro Ser Arg Gln Val Asp Thr Leu Asp His Phe Gln Lys
            245             250             255

Cys Phe Leu Ile Leu Lys Leu His His Gln Arg Val Asp Ser Ser Lys
            260             265             270

Ser Asn Gln Gln Glu Gly Lys Thr Trp Lys Ala Ile Arg Val Asp Leu
        275             280             285

Val Met Cys Pro Tyr Glu Asn Arg Ala Phe Ala Leu Leu Gly Trp Thr
    290             295             300

Gly Ser Pro Gln Phe Asn Arg Asp Leu Arg Arg Tyr Ala Thr His Glu
305             310             315             320

Arg Lys Met Met Leu Asp Asn His Ala Leu Tyr Asp Lys Thr Lys Arg
            325             330             335

Val Phe Leu Glu Ala Glu Ser Glu Glu Glu Ile Phe Ala His Leu Gly
            340             345             350

Leu Asp Tyr Ile Glu Pro Trp Glu Arg Asn Ala
            355             360
```

```
<210> SEQ ID NO 28
<211> LENGTH: 379
<212> TYPE: PRT
<213> ORGANISM: Artificial Sequence
<220> FEATURE:
<223> OTHER INFORMATION: ii-ell-40 with His tag

<400> SEQUENCE: 28
```

```
Met Ala Ser Ser His His His His His His Ser Ser Gly Ser Glu Asn
1               5               10              15

Val Ala Thr Val Ser Glu Tyr Ala Cys Gln Arg Arg Thr Thr Leu Asn
            20              25              30

Asn Tyr Asn Glu Leu Phe Thr Arg Ala Leu Asp Ile Leu Ala Glu Asn
        35              40              45

Asp Glu Phe Arg Glu Asn Glu Glu Ser Arg Asp Ala Phe Arg Arg Ala
    50              55              60

Ser Ser Val Leu Lys Ser Leu Pro Phe Pro Ile Thr Ser Met Lys Asp
65              70              75              80

Thr Glu Gly Ile Pro Cys Leu Gly Asp Lys Val Lys Arg Ile Ile Glu
            85              90              95

Glu Ile Ile Glu Asp Gly Glu Ser Ser Glu Val Lys Ala Val Leu Asn
            100             105             110

Asp Glu Arg Tyr Lys Ala Phe Lys Leu Phe Thr Ser Val Phe Gly Val
        115             120             125

Gly Arg Lys Thr Ala Glu Lys Trp Phe Arg Met Gly Phe Arg Thr Leu
    130             135             140

Glu Lys Ile Arg Ser Asp Lys Ser Leu Arg Phe Thr Gln Met Gln Lys
145             150             155             160
```

-continued

```
Ala Gly Phe Leu Tyr Tyr Glu Asp Leu Val Ser Gly Val Thr Arg Ala
            165                 170                 175

Glu Ala Glu Ala Val Gly Val Leu Val Lys Glu Ala Val Trp Ala Phe
            180                 185                 190

Leu Pro Asp Ala Phe Val Thr Met Thr Gly Gly Phe Arg Leu Gly Lys
            195                 200                 205

Lys Ile Gly His Asp Val Asp Phe Leu Ile Thr Ser Pro Gly Ser Ala
        210                 215                 220

Glu Asp Glu Glu Gln Leu Leu Pro Lys Val Ile Asn Leu Trp Glu Lys
225                 230                 235                 240

Lys Gly Leu Leu Leu Tyr Tyr Asp Leu Val Glu Ser Thr Phe Glu Lys
            245                 250                 255

Phe Lys Leu Pro Ser Arg Gln Val Asp Thr Leu Asp His Phe Gln Lys
            260                 265                 270

Cys Phe Leu Ile Leu Lys Leu His His Gln Arg Val Asp Ser Ser Lys
        275                 280                 285

Ser Asn Gln Gln Glu Gly Lys Thr Trp Lys Ala Ile Arg Val Asp Leu
    290                 295                 300

Val Met Cys Pro Tyr Glu Asn Arg Ala Phe Ala Leu Leu Gly Trp Thr
305                 310                 315                 320

Gly Ser Pro Gln Phe Asn Arg Asp Leu Arg Arg Tyr Ala Thr His Glu
            325                 330                 335

Arg Lys Met Met Leu Asp Asn His Ala Leu Tyr Asp Lys Thr Lys Arg
            340                 345                 350

Val Phe Leu Glu Ala Glu Ser Glu Glu Glu Ile Phe Ala His Leu Gly
            355                 360                 365

Leu Asp Tyr Ile Glu Pro Trp Glu Arg Asn Ala
    370                 375

<210> SEQ ID NO 29
<211> LENGTH: 363
<212> TYPE: PRT
<213> ORGANISM: Artificial Sequence
<220> FEATURE:
<223> OTHER INFORMATION: 9-40 without His tag

<400> SEQUENCE: 29

Val Ala Thr Val Ser Glu Tyr Ala Cys Gln Arg Arg Thr Thr Leu Asn
1               5                   10                  15

Asn Tyr Asn Glu Leu Phe Thr Arg Ala Leu Asp Ile Leu Ala Glu Asn
            20                  25                  30

Asp Glu Phe Arg Glu Asn Glu Glu Ser Arg Asp Ala Phe Arg Arg Ala
        35                  40                  45

Ser Ser Val Leu Lys Ser Leu Pro Phe Pro Ile Thr Ser Met Lys Asp
    50                  55                  60

Thr Glu Gly Ile Pro Cys Leu Gly Asp Lys Val Lys Arg Ile Ile Glu
65                  70                  75                  80

Glu Ile Ile Glu Asp Gly Glu Ser Ser Glu Val Lys Ala Val Leu Asn
            85                  90                  95

Asp Glu Arg Tyr Lys Ala Phe Lys Leu Phe Thr Ser Val Phe Gly Val
            100                 105                 110

Gly Arg Lys Thr Ala Glu Lys Trp Phe Arg Met Gly Phe Arg Thr Leu
        115                 120                 125

Glu Lys Ile Arg Ser Asp Lys Ser Leu Arg Phe Thr Gln Met Gln Lys
    130                 135                 140
```

-continued

```
Ala Gly Phe Leu Tyr Tyr Glu Asp Leu Val Ser Gly Val Thr Arg Ala
145                 150                 155                 160

Glu Ala Glu Ala Val Gly Val Leu Val Lys Glu Ala Val Trp Ala Phe
                165                 170                 175

Leu Pro Asp Ala Phe Val Thr Met Thr Gly Gly Phe Arg Leu Gly Lys
            180                 185                 190

Lys Ile Gly His Asp Val Asp Phe Leu Ile Thr Ser Pro Gly Ser Ala
            195                 200                 205

Glu Asp Glu Glu Gln Leu Leu Pro Lys Val Ile Asn Leu Trp Glu Lys
        210                 215                 220

Lys Gly Leu Leu Leu Tyr Tyr Asp Leu Val Glu Ser Thr Phe Glu Lys
225                 230                 235                 240

Phe Lys Leu Pro Ser Arg Gln Val Asp Thr Leu Asp His Phe Gln Lys
                245                 250                 255

Cys Phe Leu Ile Leu Lys Leu His His Gln Arg Val Asp Ser Ser Lys
                260                 265                 270

Ser Asn Gln Gln Glu Gly Lys Thr Trp Lys Ala Ile Arg Val Asp Leu
            275                 280                 285

Val Met Cys Pro Tyr Glu Asn Arg Ala Phe Ala Leu Leu Gly Trp Thr
    290                 295                 300

Gly Ser Pro Gln Phe Asn Arg Asp Leu Arg Arg Tyr Ala Thr His Glu
305                 310                 315                 320

Arg Lys Met Met Leu Asp Asn His Ala Leu Tyr Asp Lys Thr Lys Arg
                325                 330                 335

Val Phe Leu Glu Ala Glu Ser Glu Glu Glu Ile Phe Ala His Leu Gly
            340                 345                 350

Leu Asp Tyr Ile Glu Pro Trp Glu Arg Asn Ala
        355                 360
```

```
<210> SEQ ID NO 30
<211> LENGTH: 379
<212> TYPE: PRT
<213> ORGANISM: Artificial Sequence
<220> FEATURE:
<223> OTHER INFORMATION: 9-40 with His tag

<400> SEQUENCE: 30
```

```
Met Ala Ser Ser His His His His His His Ser Ser Gly Ser Glu Asn
1               5                   10                  15

Val Ala Thr Val Ser Glu Tyr Ala Cys Gln Arg Arg Thr Thr Leu Asn
                20                  25                  30

Asn Tyr Asn Glu Leu Phe Thr Arg Ala Leu Asp Ile Leu Ala Glu Asn
            35                  40                  45

Asp Glu Phe Arg Glu Asn Glu Glu Ser Arg Asp Ala Phe Arg Arg Ala
        50                  55                  60

Ser Ser Val Leu Lys Ser Leu Pro Phe Pro Ile Thr Ser Met Lys Asp
65                  70                  75                  80

Thr Glu Gly Ile Pro Cys Leu Gly Asp Lys Val Lys Arg Ile Ile Glu
                85                  90                  95

Glu Ile Ile Glu Asp Gly Glu Ser Ser Glu Val Lys Ala Val Leu Asn
            100                 105                 110

Asp Glu Arg Tyr Lys Ala Phe Lys Leu Phe Thr Ser Val Phe Gly Val
        115                 120                 125

Gly Arg Lys Thr Ala Glu Lys Trp Phe Arg Met Gly Phe Arg Thr Leu
    130                 135                 140
```

```
Glu Lys Ile Arg Ser Asp Lys Ser Leu Arg Phe Thr Gln Met Gln Lys
145             150             155             160

Ala Gly Phe Leu Tyr Tyr Glu Asp Leu Val Ser Gly Val Thr Arg Ala
        165             170             175

Glu Ala Glu Ala Val Gly Val Leu Val Lys Glu Ala Val Trp Ala Phe
        180             185             190

Leu Pro Asp Ala Phe Val Thr Met Thr Gly Gly Phe Arg Leu Gly Lys
        195             200             205

Lys Ile Gly His Asp Val Asp Phe Leu Ile Thr Ser Pro Gly Ser Ala
    210             215             220

Glu Asp Glu Glu Gln Leu Leu Pro Lys Val Ile Asn Leu Trp Glu Lys
225             230             235             240

Lys Gly Leu Leu Leu Tyr Tyr Asp Leu Val Glu Ser Thr Phe Glu Lys
        245             250             255

Phe Lys Leu Pro Ser Arg Gln Val Asp Thr Leu Asp His Phe Gln Lys
        260             265             270

Cys Phe Leu Ile Leu Lys Leu His His Gln Arg Val Asp Ser Ser Lys
        275             280             285

Ser Asn Gln Gln Glu Gly Lys Thr Trp Lys Ala Ile Arg Val Asp Leu
    290             295             300

Val Met Cys Pro Tyr Glu Asn Arg Ala Phe Ala Leu Leu Gly Trp Thr
305             310             315             320

Gly Ser Pro Gln Phe Asn Arg Asp Leu Arg Arg Tyr Ala Thr His Glu
        325             330             335

Arg Lys Met Met Leu Asp Asn His Ala Leu Tyr Asp Lys Thr Lys Arg
        340             345             350

Val Phe Leu Glu Ala Glu Ser Glu Glu Glu Ile Phe Ala His Leu Gly
        355             360             365

Leu Asp Tyr Ile Glu Pro Trp Glu Arg Asn Ala
    370             375
```

METHOD AND APPARATUS FOR ENZYMATIC SYNTHESIS OF POLYNUCLEOTIDES

Interest in enzymatic approaches to polynucleotide synthesis has recently increased not only because of increased demand for synthetic polynucleotides in many areas, such as synthetic biology, CRISPR-Cas9 applications, and high-throughput sequencing, but also because of the limitations of chemical approaches to polynucleotide synthesis, such as upper limits on product length and the use and needed disposal of organic solvents, Jensen et al, Biochemistry, 57: 1821-1832 (2018). Enzymatic synthesis is attractive because of its specificity and efficiency and because of its use of mild aqueous reaction conditions which eliminates the need for handling hazardous wastes.

Currently, most enzymatic approaches employ template-free polymerases to repeatedly add 3'-O-blocked nucleoside triphosphates to a single stranded initiator or an elongated strand attached to a support followed by deblocking until a polynucleotide of the desired sequence is obtained. Unfortunately, however, template-free polymerases often have sequence-specific inefficiencies in their coupling yields. That is, the sequence at the 3' end of a growing strand where nucleotide coupling occurs may affect the coupling efficiency under a given set of reaction conditions and times. This makes it difficult or impossible to obtain uniform product yields in parallel synthesis operations whenever the same reaction times are used for all reaction chambers.

In view of the above, parallel synthesis of polynucleotides using template-free polymerases would be advanced if methods and apparatus were available which were capable of minimizing product yield differences due to sequence-specific coupling inefficiencies.

SUMMARY OF THE INVENTION

The invention is directed to methods and devices, including microfluidic devices, for synthesizing in parallel a plurality of polynucleotides in separate reaction chambers.

More particularly, the present invention relates to a method for synthesizing with a template-free polymerase a plurality of polynucleotides each with a predetermined sequence, wherein the template-free polymerase has reduced coupling efficiency at one or more inefficiency motifs, the method comprising the steps of: (a) providing a reaction chamber for each polynucleotide of the plurality, each reaction chamber having disposed therein a synthesis support with initiators attached, wherein each initiator has a free 3'-hydroxyl, and wherein each reaction chamber has an inlet and an outlet and a filter that retains the synthesis support and that is operationally associated with the outlet so that reaction solutions exiting the reaction chamber pass through the filter; (b) providing a waste manifold operationally associated with the outlets of the reaction chambers so that whenever a positive pressure differential is created between the reaction chambers and the waste manifold, reaction solutions are removed from the reaction chambers; (c) repeating for each reaction chamber, until a polynucleotide of such reaction chamber is complete, cycles of the following reaction steps: (i) contacting in a coupling solution the initiator or deprotected elongated fragments with a 3'-protected nucleoside triphosphate and a template-free polymerase so that initiators or deprotected elongated fragments are elongated by the 3'-protected nucleoside triphosphate to form 3'-protected elongated fragments, (ii) deprotecting the 3'-protected elongated fragments with a deprotection solution, and (iii) applying a pressure differential between the reaction chambers and the waste manifold to remove solutions from the reaction chambers; wherein the kind of 3'-protected nucleoside triphosphate contacted in step (i) in a reaction chamber is determined by the polynucleotide sequence of the reaction chamber, and wherein, prior to each cycle, one or more short cycles of step (i) is carried out in a reaction chamber whenever an inefficiency motif is present at a 3' end of a deprotected elongated fragment of such reaction chamber. As explained more fully below, an efficiency motif is a sequence segment at the 3' end of an elongated fragment that causes the template-free polymerase to have a reduced efficiency in coupling a nucleotide monomer to the elongated fragment. In some embodiments, template-free polymerases comprise terminal deoxynucleotidyltransferases (TdTs). In some embodiments employing TdTs disclosed herein, inefficiency motifs comprise 3-mer sequences selected from the set comprising CCA, CTA, GCA, GTA and CCT. In other embodiments, such set comprises CCA and CTA. In other embodiments, inefficiency motifs of a template-free polymerase are identified, for example, as described below, so that the method and apparatus of the invention can be implemented.

The present invention also relates to an apparatus for synthesizing with a template-free polymerase a plurality of polynucleotides each with a predetermined sequence, wherein the template-free polymerase has reduced coupling efficiency at one or more inefficiency motifs, the apparatus comprising: (a) a plurality of reaction chambers, each reaction chamber having disposed therein a synthesis support with initiators attached, wherein each initiator has a free 3'-hydroxyl, and wherein each reaction chamber has an inlet and an outlet and a filter that retains the synthesis support and that is operationally associated with the outlet so that reaction solutions exiting the reaction chamber pass through the filter; (b) a waste manifold operationally associated with the outlets of the reaction chambers such that reaction solutions are removed from the reaction chambers and enter the waste manifold whenever a positive pressure differential is established between the reaction chambers and the waste manifold; (c) a fluid delivery system for delivering reaction solutions to the reaction chambers of the array; (d) a user interface for accepting nucleotide sequences of polynucleotides to be synthesized and inefficiency motif data; (e) a control system operationally associated with the user interface, the plurality of reaction chambers, the fluid delivery system and the waste manifold, wherein the control system determines for each polynucleotide a number and position of each inefficiency motif and assigns each polynucleotide to a reaction chamber for synthesis, and wherein for each reaction chamber, until the polynucleotide thereof is complete, the control system directs repeated steps of: (i) delivering a coupling solution to the initiator oligonucleotides or deprotected elongated fragments, the coupling solution containing a 3'-protected nucleoside triphosphate and a template-free polymerase under coupling conditions to allow initiator oligonucleotides or deprotected elongated fragments to be elongated by the 3'-protected nucleoside triphosphate to form 3'-protected elongated fragments, (ii) delivering a deprotection solution to the reaction chambers so that the 3'-protected elongated fragments are deprotected, and (iii) producing a pressure differential between the reaction chambers and the waste manifold to remove coupling and/or deprotection solutions from the reaction chambers; wherein the kind of 3'-protected nucleoside triphosphate contacted in step (i) in a reaction chamber is determined by the predetermined sequence for the reaction chamber, and wherein, prior to each cycle, one or more short cycles of step (i) are performed in a reaction chamber whenever an inefficiency motif is present at a 3' end of a deprotected elongated fragment of such reaction chamber.

As above, in some embodiments of the apparatus of the invention, template-free polymerases comprise terminal deoxynucleotidyltransferases (TdTs). In further embodiments employing TdTs disclosed herein, inefficiency motifs comprise 3-mer sequences selected from the set comprising CCA, CTA, GCA, GTA and CCT. In other embodiments, such set comprises CCA and CTA.

The apparatus of the present invention is particularly suited to implement the method for synthesizing with a template-free polymerase a plurality of polynucleotides each with a predetermined sequence, wherein the template-free polymerase has reduced coupling efficiency at one or more inefficiency motifs of the present invention. The present invention also relates to a kit for synthesizing with a template-free polymerase a plurality of polynucleotides each with a predetermined sequence, comprising the apparatus of the present invention and 3'-protected nucleoside triphosphates and/or a template-free polymerase and/or coupling solution and/or deprotection solution.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

DETAILED DESCRIPTION OF THE INVENTION

Figure 1:
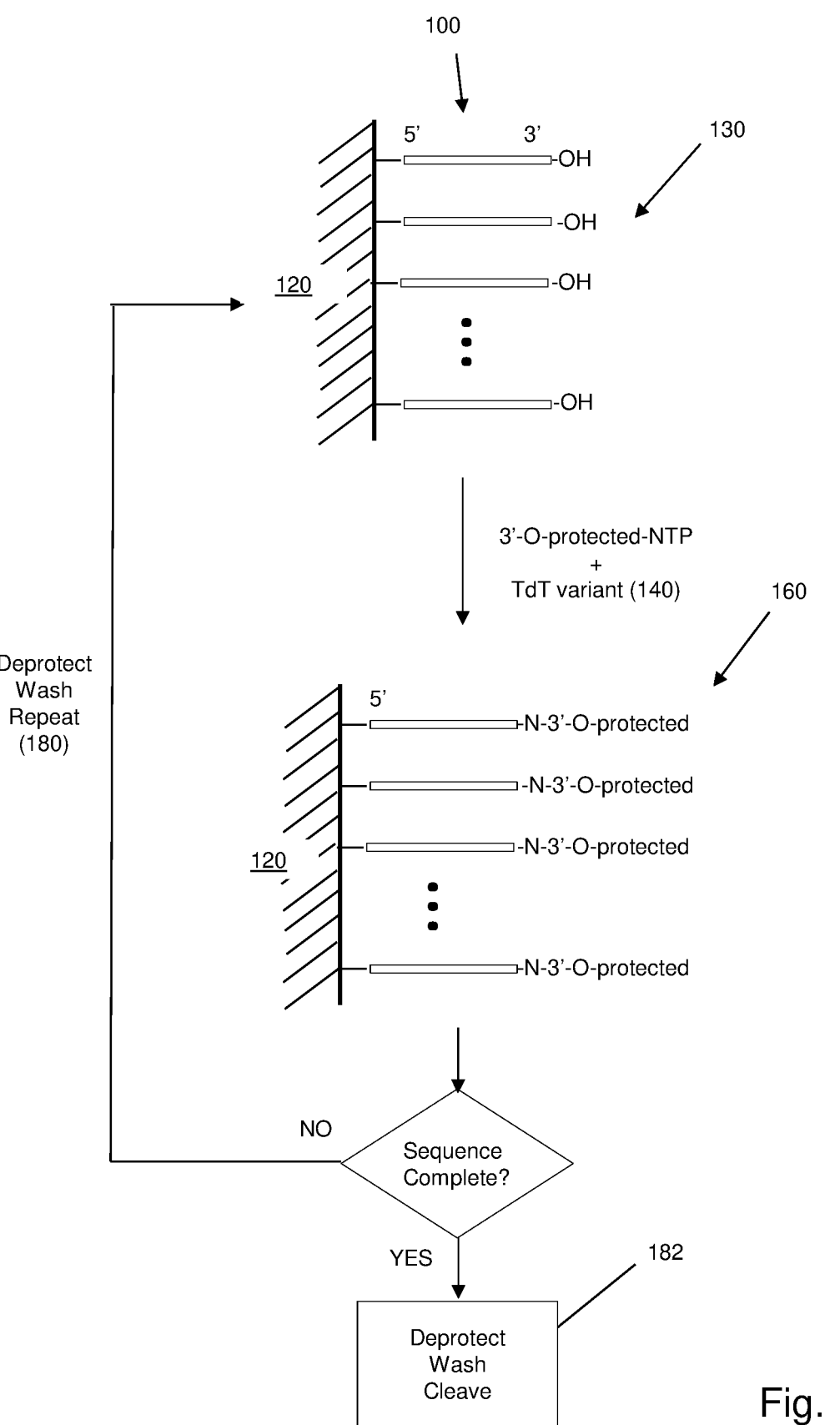
FIG. 1 illustrates diagrammatically the basic steps of enzymatic synthesis of a polynucleotide.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The practice of the present invention may employ, unless otherwise indicated, conventional techniques and descriptions of organic chemistry, molecular biology (including recombinant techniques), cell biology, and biochemistry, which are within the skill of the art. Such conventional techniques may include, but are not limited to, preparation and use of synthetic peptides, synthetic polynucleotides, monoclonal antibodies, nucleic acid cloning, amplification, sequencing and analysis, and related techniques. Protocols for such conventional techniques can be found in product literature from manufacturers and in standard laboratory manuals, such as Genome Analysis: A Laboratory Manual Series (Vols. I-IV); PCR Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

The invention is directed to methods and apparatus for parallel enzymatic synthesis of polynucleotides in an array of reaction chambers using a template-free polymerase that has sequence-dependent coupling efficiencies. Each reaction chamber of the array has an inlet and an outlet and associated with each outlet is a filter which serves to retain solid supports, e.g. beads, in the reaction chamber whenever solutions are removed through the outlet. In some embodiments, the array of reaction chambers is a planar array of microwells operationally associated with a waste manifold that allows simultaneous removal of reaction solutions (e.g., coupling solution and/or deprotection solution) from the microwells by application of a pressure differential between the microwells and the manifold.

Sequence segments of a polynucleotide at which a given template-free polymerase has reduced coupling efficiency are referred to herein as the "inefficiency motifs" of the polymerase. Whenever an inefficiency motif appears at the 3' end of the growing chain (or elongated fragment), reduced coupling efficiency occurs. Such reduced coupling efficiency may be manifested by an increase in nucleotide deletions next to the 3' end of the inefficiency motifs in completed products, compared to completed products not containing an inefficiency motif at the same location, when the coupling reaction time is the same for all reactions. The phenomena is illustrated for two terminal deoxynucleotidyl transferase (TdT) variants in FIGS. 3A-3B. The magnitude of the coupling inefficiency of a template-free polymerase can vary widely so that implementation of the invention depends on such magnitude and the desired purity and yield of the final products. In some embodiments, an inefficiency motif is identified as a 3'-terminal sequence the reduces coupling efficiency by 10 percent or more as compared to the average coupling efficiency over all 3'-terminal sequences of the same length. In other embodiments, an inefficiency motif is identified as a 3'-terminal sequence the reduces coupling efficiency by 25 percent or more as compared to the average coupling efficiency over all 3'-terminal sequences of the same length. In still other embodiments, an inefficiency motif is identified as a 3'-terminal sequence the reduces coupling efficiency by 50 percent or more as compared to the average coupling efficiency over all 3'-terminal sequences of the same length.

In accordance with methods and apparatus of the invention, inefficiency motifs characteristic of a template-free polymerase are located in each of the plurality of polynucleotides to be synthesized. This information is then used to insert so-called "short" coupling cycles into the synthesis plan of each polynucleotide to provide extra time for the reactions at the inefficiency motifs to take place, while not affecting the coupling times of reactions that do not involve inefficiency motifs. As described more fully below, a regular cycle in the enzymatic synthesis of a polynucleotide (as illustrated in FIG. 1) comprises the steps of (i) coupling a 3'-O-reversibly blocked-nucleoside triphosphate to a free 3'-OH of a growing chain (or an initiator in the first cycle), (ii) deblocking the 3'-OH of the added nucleotide, and (iii) washing. A short cycle may comprise a variety of steps, but the key feature is that it includes a coupling step without any deblocking step, thereby permitting a further accumulation of couplings to free 3'—OH groups in the reaction chamber where the short cycle is implemented.

An apparatus of the invention comprises a fluid delivery system for delivering reaction solutions to reaction chambers under programmed control so that the appropriate reaction solutions (e.g. "A", "C", "G" or "T" coupling reagents or solutions, wash solutions, deprotection or deblocking solution, etc.) get delivered to the appropriate reaction chamber at the appropriate times in order to produce polynucleotides of the desired sequences. After the plurality of polynucleotide sequences are available, for example, by entering them through a user interface, a reaction chamber is assigned to each polynucleotide and a sequence of regular and short cycles is determined for each polynucleotide. This determination includes analyzing the polynucleotide sequences to identify the number and locations of inefficiency motifs and (consequently) the locations for inserting one or more short cycles for the synthesis plan of the polynucleotide. The term "synthesis plan" in reference to a polynucleotide means the sequence of regular and short cycles used in a method or in an apparatus to synthesize such polynucleotide. A synthesis plan for a hypothetical polynucleotide (SEQ ID NO: 1) is illustrated in FIG. 2C.

Both regular and short cycles have the same number of steps with the same duration. After each step in either type of cycle, reaction solutions are removed from all of the reaction chambers via their outlets. In some embodiments, the regular and short cycles differ only in the activities that take place in the reaction chambers between removals of reaction solutions. In accordance with methods and apparatus of the invention, reaction solutions are removed from reaction chambers by generating a pressure differential between the reaction chambers and a waste manifold operationally associated with the outlets of the array of reaction chambers. In some embodiments, such a pressure differential is generated by connecting the waste manifold to a vacuum source, so that the vacuum pulls liquids from the chambers through their filters and outlets and into a chamber of the waste manifold and, eventually, to a waste container.

Figure 3A:
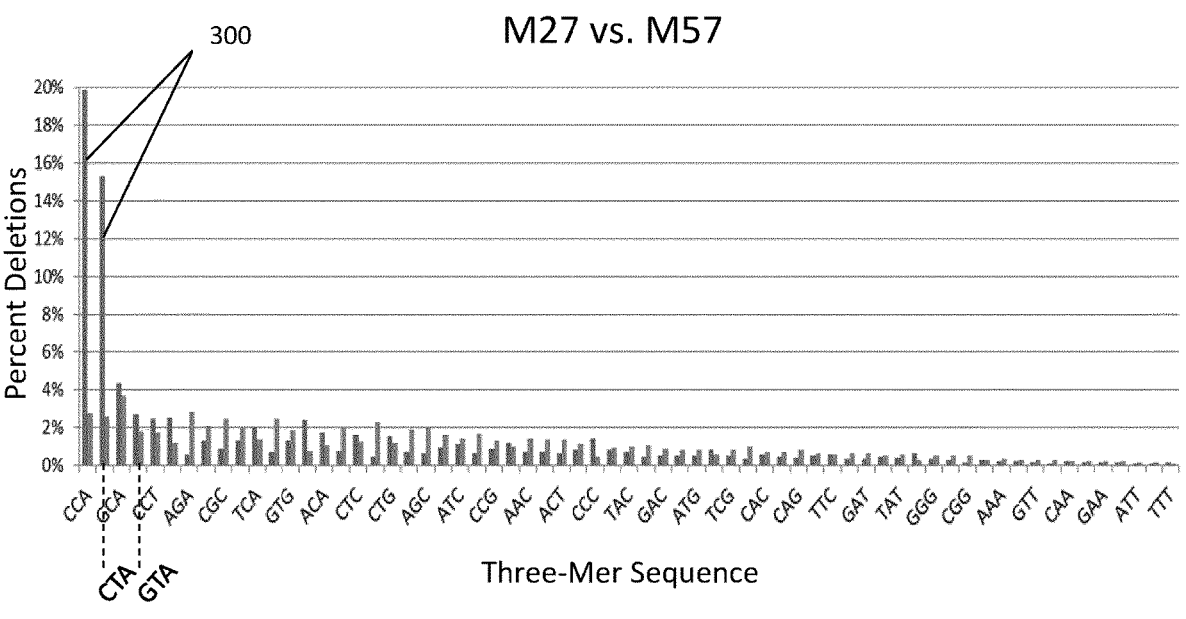
FIGS. 3A and 3B show data on relative coupling efficiencies at 3'-3-mer sequence for different TdT variants.
Figure 3B:
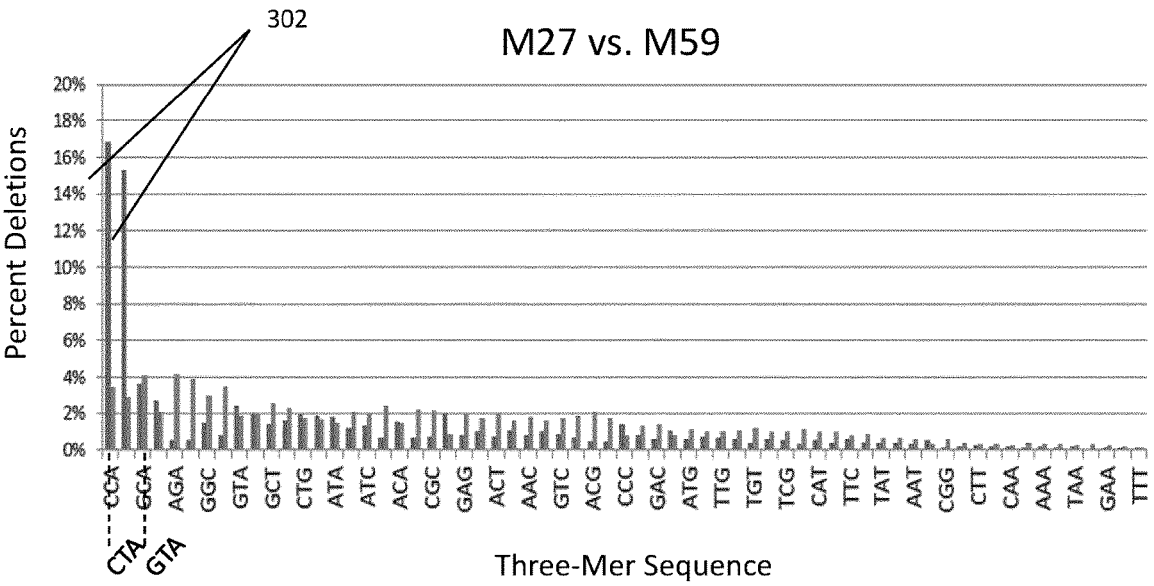

Typically, an inefficiency motif consists of from 1 to 5 nucleotides, and more usually, an inefficiency motif consists of 3 nucleotides. As explained more fully below, and as illustrated in FIGS. 3A and 3B, the inefficiency motifs of a given template-free polymerase may readily be determined by sequencing a sample of polynucleotide products synthesized using such polymerase in a standard reaction and tabulating deletions adjacent to subsequences (for example, 3-mers) in the products. This procedure also provides a measure of the coupling efficiency at every possible sequence segment of a given length at the 3' end of a growing chain. After this information is obtained, it is a design choice of one of ordinary skill in the art to select one or more inefficiency motifs (corresponding to low efficiency coupling) for implementing methods and apparatus of the invention; that is, it is a design choice of such a person to determine how much reduction in coupling efficiency to tolerate before ameliorating it by inserting one or more short cycles to provide additional coupling time. As illustrated in FIGS. 3A-3B, in some embodiments, there may be one or more inefficiency motifs for a given template-free polymerase. In other embodiments, the number of different inefficiency motifs for a given template-free polymerase may be in the range of from 1 to 6. In still other embodiments, the number of different inefficiency motifs for a given template-free polymerase may be a plurality; and in some embodiments the plurality may be in the range of from 2 to 10; or from 2 to 6; or from 2 to 4. While not wishing to be bound by theory or hypothesis, in regard to terminal deoxynucleotidyl transferases (TdTs) or related template-free polymerases, it is believed that in some embodiments, the coupling efficiency at certain sequences, especially 3-mer sequences, is proportional to the stability of the attachment of a polymerase to the 3' end of a growing chain. That is, low efficiency coupling may be due to a lack of stability of the TdT-growing chain complex, so that there are fewer such complexes available to capture monomers for coupling to a growing chain.

Figure 2A:
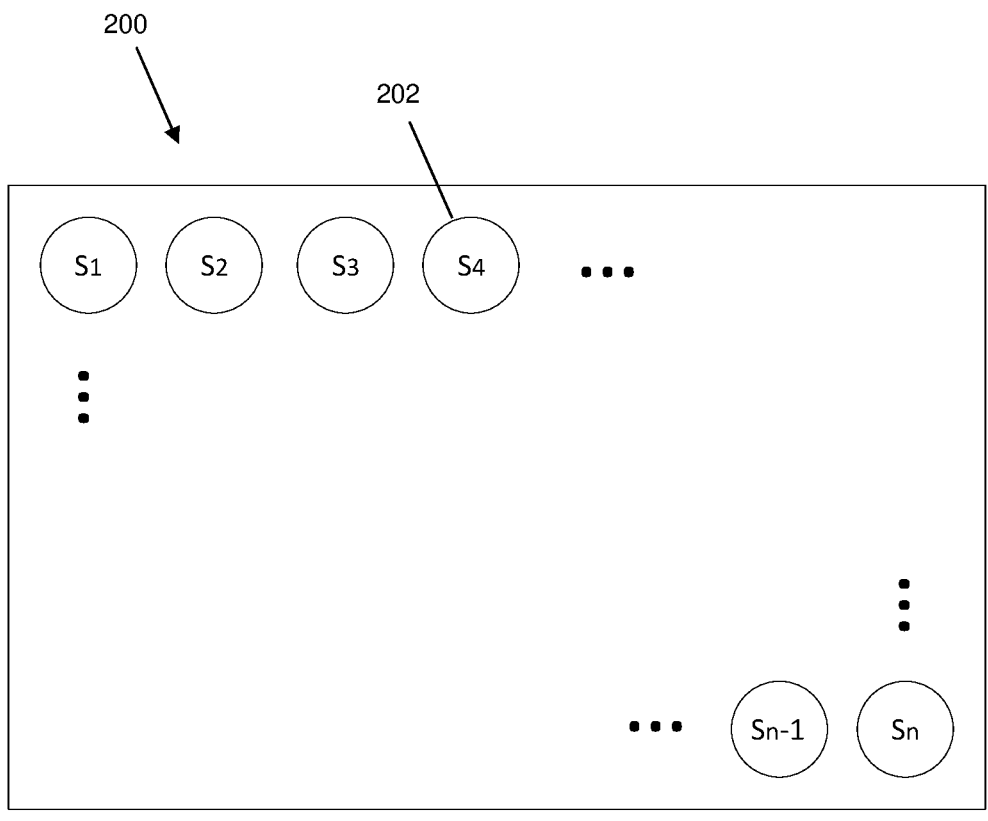
FIG. 2A illustrates an array of reaction wells, for example, each reaction well having an outlet for removing reaction fluids and each being addressable for the purpose of delivering reagents.
Figure 2B:
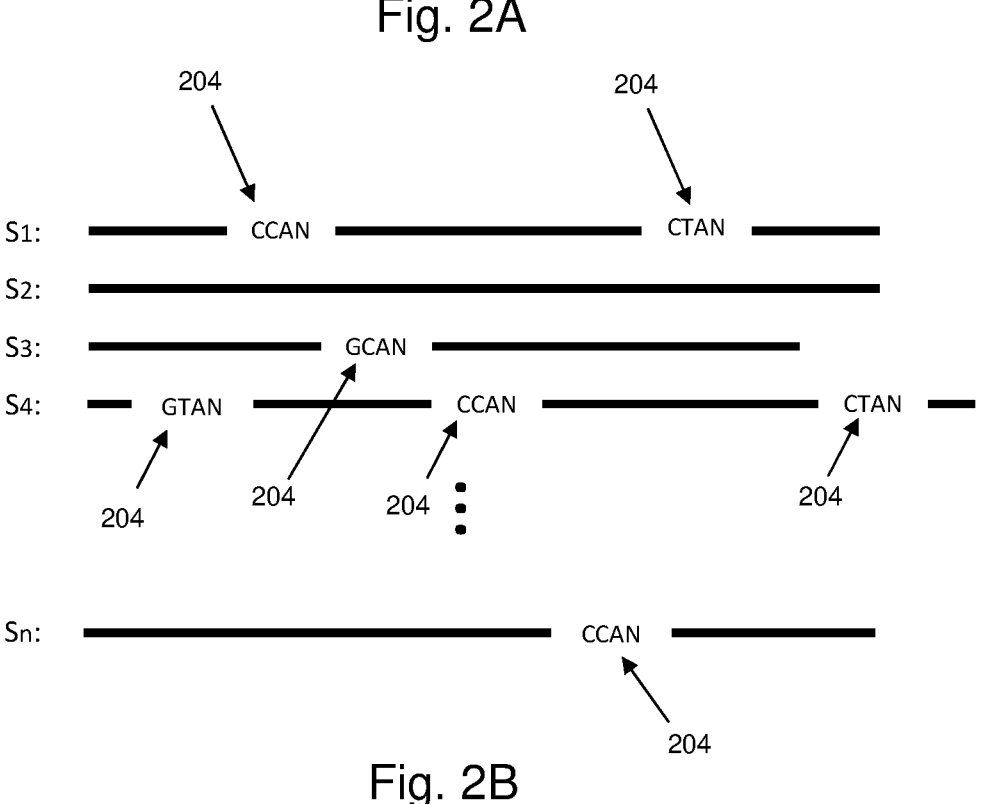
FIG. 2B illustrates a given selection of polynucleotides that may be synthesized in parallel in the reaction wells of FIG. 2A, showing for each polynucleotide the occurrences of inefficiency motifs giving rise to difficult couplings for a selected template-free polymerase, such as TdT variant. M27.
Figure 2C:
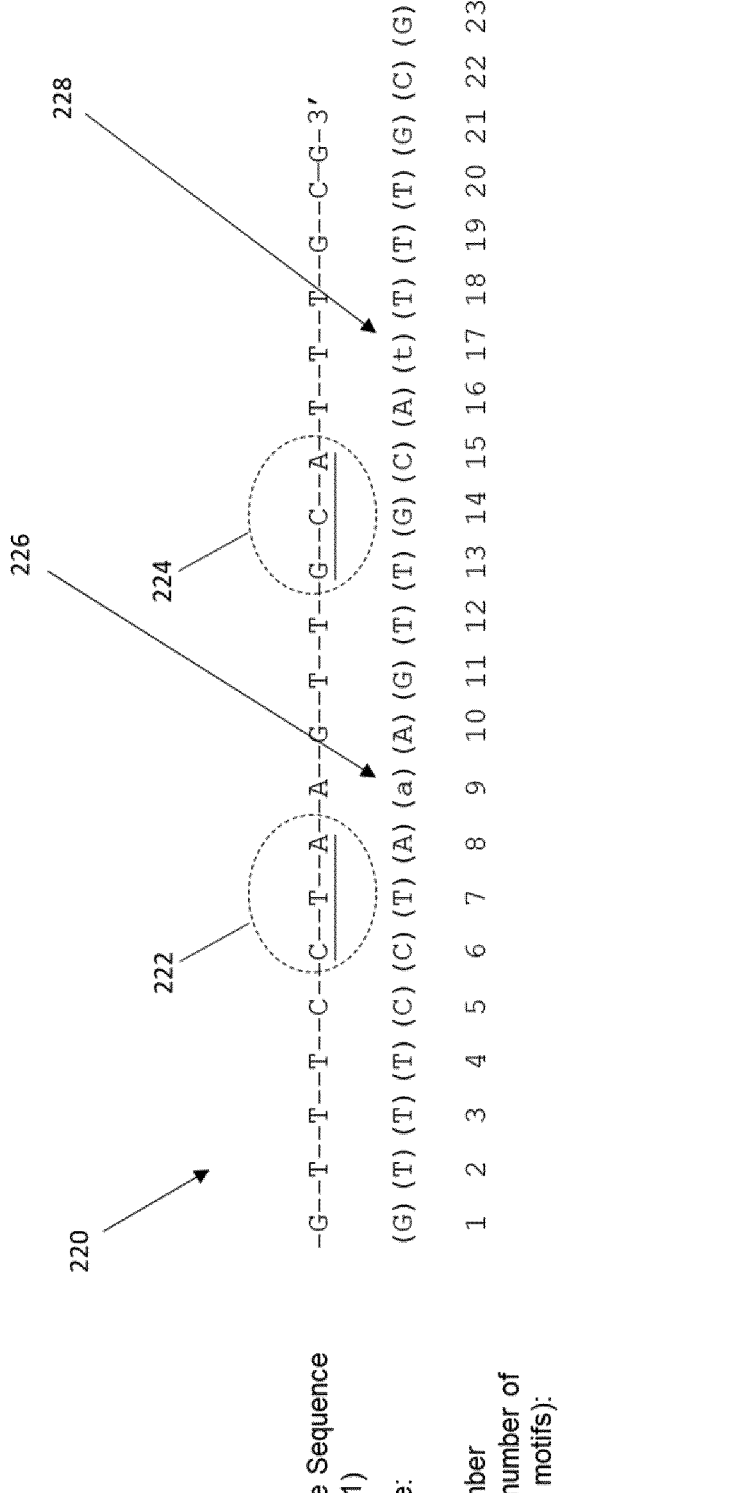
FIG. 2C illustrates the insertion of "short" synthesis cycles after the indicated inefficiency motifs, which short cycles effectively provide additional time for coupling after such inefficiency motifs.

Aspects of the present invention are illustrated in FIGS. 2A-2C. As illustrated in FIG. 2A, more than one polynucleotide are synthesized in planar array (200) of reaction chambers (202) that may be label $S_1$ through $S_n$ as shown. In some embodiments, each polynucleotide is synthesized in a separate reaction chamber. As illustrated in FIG. 2B, after user input, the sequence of each polynucleotide is analyzed to determine the identities and positions of inefficiency motifs (204) (in this example, CCA, CTA, and GCA) and the nucleotides immediately 3' of them. This determines the numbers and positions at which short cycles will be inserted into the synthesis plan for each polynucleotide. In some embodiments, one or more short cycles are inserted after (i.e., 3' of) each inefficiency motif. In some embodiments, the number or type of short cycles inserted may depend on the inefficiency motif. In some embodiments, a single short cycle is inserted after each inefficiency motif. As noted above, in some embodiments, both regular and short cycles comprise three steps of equal duration and after each step (or as part of each step) a pressure differential is generated between the reaction chambers and a waste manifold to remove reaction solutions (if any) from the reaction chambers. In some embodiments, such pressure differential is created by connecting the waste manifold to a conventional vacuum source. Typically vacuum is applied for 10-30 seconds between the steps. A regular cycle may be represented as follows:

Steps of Regular Cycle

| Step | Action | Duration |
|------|--------|----------|
| (i) | Couple | $t_1$ |
| (ii) | Deprotect | $t_2$ |
| (iii) | Wash-Remove RS | $t_3$ |

As shown above, the coupling reaction solution (RS) remains in the reaction chamber and the deblocking solution is simply added to it in step (ii). In some embodiments, a wash step to remove reaction solution may be performed after the coupling step and before the deprotection step. As noted above, short cycles may have a variety of formats illustrated by the following tables (which are not intended to be exhaustive).

Steps of Short Cycle (format 1)

| Step | Action | Duration |
| --- | --- | --- |
| (i) | Couple-Remove RS | $t_1$ |
| (ii) | Couple-Remove RS | $t_2$ |
| (iii) | Couple-Remove RS | $t_3$ |

Steps of Short Cycle (format 2)

| Step | Action | Duration |
| --- | --- | --- |
| (i) | Couple-Remove RS | $t_1$ |
| (ii) | Couple-Remove RS | $t_2$ |
| (iii) | Wash or skip-Remove RS | $t_3$ |

Steps of Short Cycle (format 3)

| Step | Action | Duration |
| --- | --- | --- |
| (i) | Couple-Remove RS | $t_1$ |
| (ii) | Wash or skip-Remove RS | $t_2$ |
| (iii) | Wash or skip-Remove RS | $t_3$ |

Steps of Short Cycle (format 4)

| Step | Action | Duration |
| --- | --- | --- |
| (i) | Couple-Remove RS | $t_1$ |
| (ii) | Wash-Remove RS | $t_2$ |
| (iii) | Couple-Remove RS | $t_3$ |

In particular embodiments, further steps may be performed either in each cycle or periodically during the synthesis process. For example, from time to time, if enzyme accumulation arises, for example, by template-free polymerase sticking to surfaces, such as reaction chamber walls, the filter surfaces or pores so as to cause blockage that inhibits fluid transfer, steps of protease treatment may be employed. The reaction times or durations, $t_1$, $t_2$ and $t_3$ may vary widely depending on particular embodiments in which, for example, different template-free polymerases, reaction temperatures, reaction buffers, monomers, deprotection solutions, and the like, are employed.

The above process of inserting short cycles is illustrated in FIG. 2C for hypothetical 21-mer sequence (220) (SEQ ID NO: 1). Analysis of 21-mer (220) identifies two inefficiency motifs: CTA (222) and GCA (224). A synthesis plan for the polynucleotide is shown in the line below where a regular cycle is indicated by "(N)" with N=A, C, G or T, a short cycle is indicated by "(n)" with n=a, c, g or t, and the letter indicates the kind of nucleotide added in the cycle. Because of the inefficiency motifs, two short cycles are added in this example (226 and 228) each inserted immediately after, or 3' of, an inefficiency motif. The selection of whether one, two, three, or more short cycles are inserted and the format of short cycle are design choices of one of ordinary skill in the art which depend at least in part on the particular template-free polymerase employed, and particularly, on the magnitude of the reduction in coupling efficiency after a inefficiency motif. Other factors may include the concentration or activity of the polymerases employed.

A wide variety of apparatus may be constructed or adapted for use to perform steps of methods of the invention. Extensive guidance for this purpose is available in the literature of automated chemical synthesis and analysis, e.g. Miertus et al, editors, Combinatorial Chemistry and Technologies: Methods and Applications, Second Edition (CRC Press, 2005); West et al, U.S. Pat. No. 9,103,809; Butendeich et al, J. Laboratory Automation, 18(3): 245-250 (2013); Fluent Automated Workstations (Tecan Group); Tisone et al, U.S. Pat. No. 6,063,339; Cathcart et al, U.S. Pat. No. 5,443,791; Ingenhoven et al, U.S. Pat. No. 7,529,598; Glauser et al, U.S. Pat. No. 8,580,197; Sindalar et al, Nucleic Acids Research, 23(6): 982-987 (1995); Cheng et al, Nucleic Acids Research, 30(18): e93 (2002); Skold et al, U.S. Pat. No. 5,273,718; and the like. In some embodiments, apparatus of the invention may comprise in part conventional fluid delivery robots. In other embodiments, apparatus of the invention may comprise in part inkjet fluid delivery systems.

In some embodiments, apparatus of the invention comprise the following elements: (a) a plurality of reaction chambers each having an inlet and an outlet wherein the outlet is operationally associated with a filter membrane or layer which permits solid supports to be retained in the reaction chamber when reaction solutions are removed through the outlet, (b) a waste manifold that is connectable to the plurality of reaction chambers so that when connected reaction solutions may be removed from all of the reaction chambers whenever a pressure differential is generated between the reaction chambers and the waste manifold, (c) a fluid delivery system for delivering under programmed control one or more reaction solutions to the plurality of reaction chambers, (d) a user interface for accepting nucleotide sequences of the polynucleotides to be synthesized and inefficiency motif data, and (e) a control system operationally associated with the user interface, the array of reaction chambers, the fluid delivery system and the waste manifold for (i) analyzing the entered nucleotide sequences and inefficiency motif data and determining a synthesis plan and assigning a reaction chamber for each polynucleotide, and (ii) for controlling the fluid delivery system, waste manifold and array so that for each reaction chamber, until the predetermined sequence thereof is complete, to repeat steps of: (A) delivering a coupling solution to the initiator oligonucleotides or deprotected elongated fragments, the coupling solution containing a 3'-protected nucleoside triphosphate and a template-free polymerase under coupling conditions to allow initiator oligonucleotides or deprotected elongated fragments to be elongated by the 3'-protected nucleoside triphosphate to form 3'-protected elongated fragments, (B) delivering a deprotection solution to the reaction chambers so that the 3'-protected elongated fragments are deprotected, and (C) producing a pressure differential between the reaction chambers and the waste manifold to remove deprotection solution from the reaction chambers; wherein the kind of 3'-protected nucleoside triphosphate contacted in step (A) in a reaction chamber is determined by the predetermined sequence for the reaction chamber, and wherein, prior to each cycle, one or more short cycles of step (A) are carried out in a reaction chamber whenever a inefficiency motif is present at a 3' end of a deprotected elongated fragment of such reaction chamber.

In some embodiments, after completing the synthesis of the polynucleotides further steps may be performed to cleave the completed polynucleotides from the solid supports and to purify them for applications. Such further steps may be performed either in the reaction chambers of the array or the polynucleotides still attached to the solid supports may be transferred to other reaction vessels for the performance of such further steps. Additionally, some cleavage methods may result in a released product that still requires modification to convert it into a useable product. For example, in the "endonuclease V-inosine" cleavage (described below) leaves a 5'-phosphate that must be removed for some applications. Thus, a further step of phosphatase treatment may be required.

Figure 4:
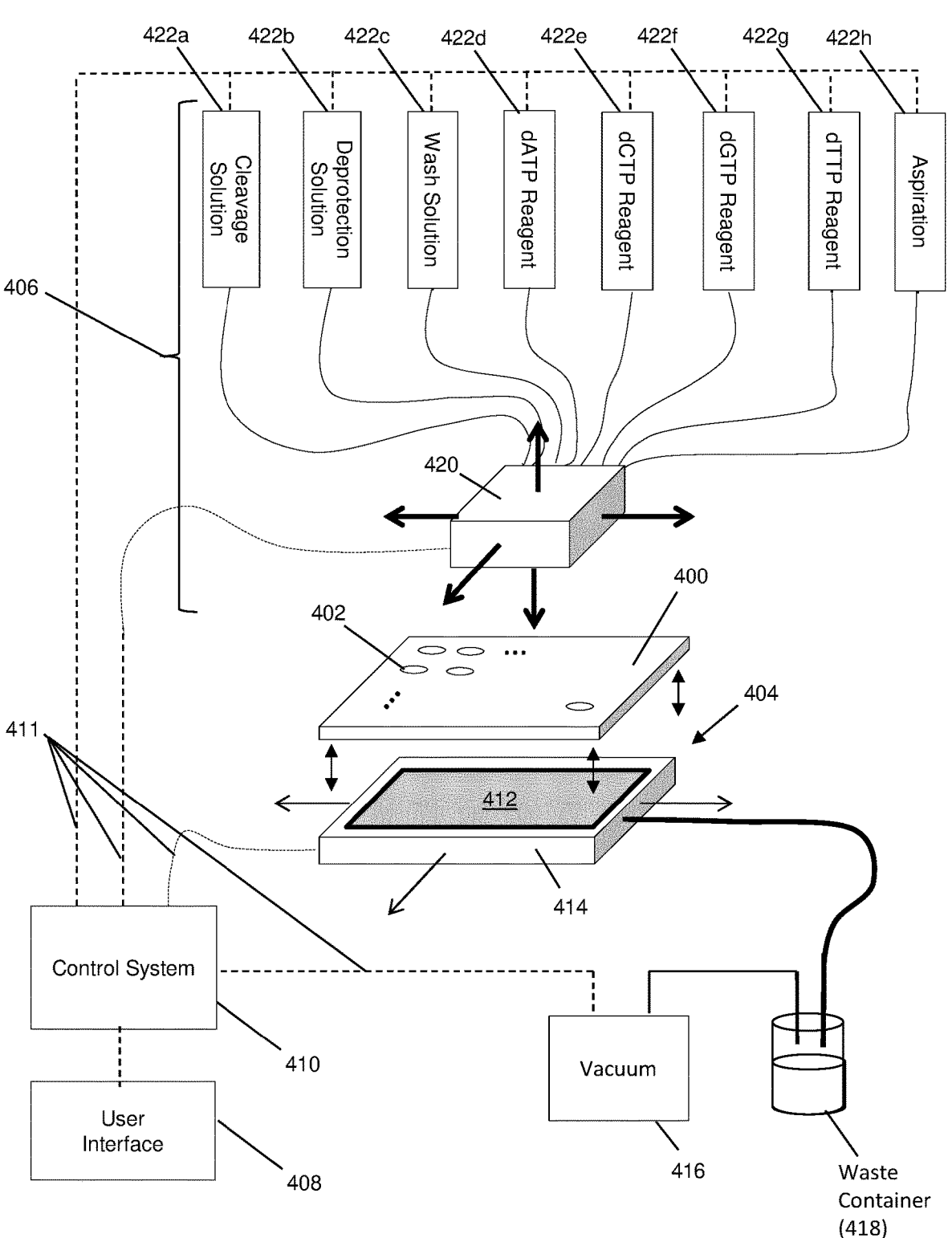
FIG. 4 illustrates an apparatus of the invention.

FIG. 4 illustrates diagrammatically elements of one embodiment of an apparatus of the invention. Such elements comprise: (a) a plurality of reaction chambers (402) in array (400); (b) waste manifold (404) which is operationally associated with reaction chambers (402) of array (400); (c) fluid delivery system (406) for delivering reaction solutions to reaction chambers (402) under programmed control; (d) user interface (408) for entering nucleotide sequences of polynucleotides and inefficiency motif data; and (e) control system (410) which (i) receives nucleotide sequence and inefficiency motif data from user interface (408), (ii) computes synthesis plans for each polynucleotide, (iii) assigns polynucleotides to reaction chambers (402) for synthesis, and (iv) controls reaction solution delivery to, and removal from, individual reaction chambers (402) by sending commands to the controllers of fluid delivery system (406), array (400) and waste manifold (404). Array (400) of reaction chambers (402) may be convention filter plates in 24-well, 96-well, 384-well, 1536-well, or similar formats, e.g. available from commercial manufacturers, such as, Pall Corp., Port Washington, NY Reaction volumes typical for such filter plates may be employed with the invention, e.g. 10-50 μL for 96-well plates, 3-10 μL for 384-well plates, 0.5-3.0 μL for 1536-well plates. Waste manifold (404) may comprise chamber (412) in body (414) that clamps sealingly to array (400) so that when chamber (412) is connected to vacuum source (416) vacuum is transmitted to outlets of all the individual reaction chambers (402) in array (400) and waste reaction solution is transferred to waste container (418). Array (400) may be moveable either with or separately from waste manifold (404). For example, fluid delivery to reaction chambers may be performed by having array (400) stationary and head (420) moveable in x, y, and z directions relative to the surface of array (400), or array (400) may be moveable in the x and y directions also, or both elements may be moveable with respect to one another in the x and y directions. Head (420) may be a framework onto which pipettes, nozzles or jets are mounted, possibly with valves and actuators. The framework, in turn, may be mounted on a robotic arm, gantry rails, or other mechanical components that permit it to be programmably translated over array (400) for delivering reaction solutions. Fluid delivery may be accomplished by a variety of methods. In some embodiments, the scale of synthesis required is an important factor. For large numbers of polynucleotides in low quantities, fluid delivery may be accomplished by inkjet methodologies or a combination of inkjet methodologies and bulk flow, e.g. bulk flow for wash or some deprotection steps. For moderate numbers of polynucleotides, e.g. in the range of from 10 to 2000, or from 10 to 1000, or from 10 to 384, fluid delivery may be accomplished by pipetting volumes in the range of 0.5 μL to 50 μL, or more, and conventional automated laboratory systems (as referenced above) may be employed. In some embodiments, fluid delivery system (406) comprises one or more reagent reservoirs (e.g. 422a-422g) and a moveable head (420). In some embodiments, fluid delivery system may also include sub-elements or even a separate head for aspirating reaction solutions from reaction chambers (402). For example, in some embodiments, it may be advantageous to transfer completed polynucleotides attached to solid supports to separate reaction chambers for cleavage and purification.

This may be accomplished by aspirating such reaction solutions from each reaction chamber in which synthesis took place and depositing the solutions in separate reaction chambers of a separate array. In other embodiments, cleavage of completed polynucleotides from solid supports may be carried out in the reaction chambers where synthesis took place using cleavage solution (422a).

As noted, control system (410) sends signals (411) to controllers that actuate elements and sub-elements of fluid delivery system (406), array (400), waste manifold (404) and vacuum source (416) in order to perform the synthesis plans determined by control system (410). In some embodiments, control system (410) may be a general purpose programmable computer running conventional instrument control software (e.g. LabVIEW, National Instruments, Austin, TX).

Determining Inefficiency Motifs of a Template-Free Polymerase

The relative efficiencies of nucleotide incorporation of a template-free polymerase as a function of the 3'-terminal sequences of a growing chain are readily determined by sequencing a sample of random-sequence products each synthesized in a standard reaction. 2-mers, 3-mers, 4-mers, and so on, of the resulting sequences are then tabulated according to how many deletions occur in the immediately adjacent 3' position. 2-mer, 3-mer or 4-mer sequences with higher numbers of deletions are candidate inefficiency motifs. As an exemplary test, twenty-four 52-mer random sequence polynucleotides may be synthesized (e.g. in duplicate or triplicate) by a template-free polymerase, such as a TdT variant. The twenty-four 52-mers may be selected as follows: each possible 4-mer is represented in the total (24×52 effective sequence length) at approximately its expected frequency, i.e. $\frac{1}{256}$, or about 4 or 5 occurrences. (That is, random sequences with skewed representations of 4-mers, such as, for example, those that just happen to be missing many 4-mers, are rejected).

Exemplary synthesis conditions for TdT. In this example, the 3'-O-blocked dNTPs are 3' NH2-dNTPs, but similar reaction conditions would hold for other reversible protecting groups. Premixes containing two times concentrated dNTP-ONH2 (1 mM), DMSO (20%) and cofactor (4 mM $CoCl_2$) and two times concentrated mutants (32 μM) are prepared separately in TY1× buffer 0.01% Tween20. For the M59 vs M27 reactions, the Tween20 is added 2× in the nucleotide premixes. The twenty-four sequences (52 mers) are synthesized in duplicates at 37° C. with M27 and either M59 or M57. Elongation time is set at 4 min. The synthesis is performed using 500 pmole of dI resin (R133) and filter plates with wwPTFE membranes (Pall Laboratory, New York). TY1× buffer contains potassium cacodylate 200 mM pH6.8, MgCl2 5 mM. dI resin R133 is a CNBr sepharose resin (GE Healthcare) coupled with 10T-dI-T initial DNA (initiator DNA) via an amino function and linker is C12. The complete initiator sequence attached to the resin is 5AmMC12/TTTTTTTTTT/dI/T.

Post synthesis processing. After synthesis, first washes are performed (1×100 μL/well H2O, 3×100 μL/well SDS/DTT, 3×100 μL/well H2O). 3×50 μL washes are performed with TH1 buffer 1× or with WLE1 buffer 1× immediately after removing the remaining liquid by vacuuming and centrifuging the plates 2 min at 2000 g. The cleavage to remove synthesized stands from the resin is performed directly after. For dI cleavage, resins are incubated with 1 μM EndoV in 50 μL reaction volume (10 mM Tris pH7.9 containing 173 mM NaCl and 50 mM MgCl2 or 10 mM Tris pH7.9 containing 50 mM KCl and 15 mM MgCl2) for 30 min, 42° C., 1250 rpm then centrifuged at 2000 g for 2 min. Resins are washed with 25 µL TH1 buffer 1× or with WLE1 buffer 1×, incubated 2 more min at 42° C., 1250 rpm and centrifuged again at 2000 g for 2 min. The recovered filtrates are transferred to 96 well PCR plate and stored at −20° C. if needed. At the end, less than 75 µL is collected from each well. TH1 buffer contains 10 mM Tris, 170 mM NaCl, 50 MgCl2 pH8. WLE1 buffer contains 10 mM Tris pH7.9, 50 mM KCl and 15 mM MgCl2.

DNA precipitation. 0.5 µL glycogen and NaAc (3M) pH 5.2 (7.5 µL) are added per well and briefly shaked. 75 µL of isopropanol are added per well and centrifuged at 3428 g for 1h15 at 4° C. The supernatants are aspirated and only 20 µL is left in each well. 180 µL of freshly prepared ethanol 80% are added per well and centrifuged at 3428 g for 30 min at 4° C. The supernatants are removed and the wash is repeated. After centrifugation, only 10 µL per well is left to be dried in Speedvac at 35° C. for 30 min. The dried DNA is resuspended in 15 µL water MB grade, after which the concentrations are measured.

Library preparation: Libraries are prepared using the Accel-NGS 1S Plus DNA Library Kit for Illumina 1 96 rxns (ozyme SW10096). The libraries are indexed using the 15 Plus Indexing Kit for Illumina (ozyme SW16024). The resulting sequence data may be displayed in tabular form or graphically, as shown in FIGS. 3A-3B, to rapidly identify inefficiency motifs.

Template-Free Enzymatic Synthesis of Oligonucleotides

Generally, methods of template-free (or equivalently, "template-independent") enzymatic DNA synthesis comprise repeated cycles of steps, such as are illustrated in FIG. 1 (for a so-called "regular" cycle), in which a predetermined nucleotide is coupled to an initiator or growing chain in each cycle. The general elements of template-free enzymatic synthesis is described in the following references: Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

Initiator polynucleotides (100) are provided, for example, attached to solid support (120), which have free 3'-hydroxyl groups (130). Solid supports may be planar solid surfaces, beads, such as magnetic beads, agarose beads, or the like. To the initiator polynucleotides (100) (or elongated initiator polynucleotides in subsequent cycles) are added a 3'-O-protected-dNTP and a template-free polymerase, such as a TdT or variant thereof (e.g. Ybert et al, WO/2017/216472; Champion et al, WO2019/135007) under conditions (140) effective for the enzymatic incorporation of the 3'-O-protected-dNTP onto the 3' end of the initiator polynucleotides (100) (or elongated initiator polynucleotides). This reaction produces elongated initiator polynucleotides whose 3'-hydroxyls are protected (160). If the elongated sequence is not complete, then another cycle of addition is implemented (180). If the elongated initiator polynucleotide contains a competed sequence, then the 3'-O-protection group may be removed, or deprotected, and the desired sequence may be cleaved from the original initiator polynucleotide (182). Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase. If the elongated initiator polynucleotide does not contain a completed sequence, then the 3'-O-protection groups are removed to expose free 3'-hydroxyls (130) and the elongated initiator polynucleotides are subjected to another cycle of nucleotide addition and deprotection.

As used herein, an "initiator" (or equivalent terms, such as, "initiating fragment," "initiator nucleic acid," "initiator oligonucleotide," or the like) usually refers to a short oligonucleotide sequence with a free 3'-hydroxyl at its end, which can be further elongated by a template-free polymerase, such as TdT. In one embodiment, the initiating fragment is a DNA initiating fragment. In an alternative embodiment, the initiating fragment is an RNA initiating fragment. In some embodiments, an initiating fragment possesses between 3 and 100 nucleotides, in particular between 3 and 20 nucleotides. In some embodiments, the initiating fragment is single-stranded. In alternative embodiments, the initiating fragment may be double-stranded. In some embodiments, an initiator oligonucleotide may be attached to a synthesis support by its 5'end; and in other embodiments, an initiator oligonucleotide may be attached indirectly to a synthesis support by forming a duplex with a complementary oligonucleotide that is directly attached to the synthesis support, e.g. through a covalent bond. In some embodiments a synthesis support is a solid support which may be a discrete region of a solid planar solid, or may be a bead.

In some embodiments, an initiator may comprise a non-nucleic acid compound having a free hydroxyl to which a TdT may couple a 3'-O-protected dNTP, e.g. Baiga, U.S. patent publications US2019/0078065 and US2019/0078126.

After synthesis is completed polynucleotides with the desired nucleotide sequence may be released from initiators and the solid supports by cleavage.

A wide variety of cleavable linkages or cleavable nucleotides may be used for this purpose. In some embodiments, cleaving the desired polynucleotide leaves a natural free 5'-hydroxyl on a cleaved strand; however, in alternative embodiments, a cleaving step may leave a moiety, e.g. a 5'-phosphate, that may be removed in a subsequent step, e.g. by phosphatase treatment. Cleaving steps may be carried out chemically, thermally, enzymatically or by photochemical methods. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage may be accomplished by providing initiators with a deoxyinosine as the penultimate 3' nucleotide, which may be cleaved by endonuclease V at the 3' end of the initiator leaving a 5'-phosphate on the released polynucleotide. Further methods for cleaving single stranded polynucleotides are disclosed in the following references, which are incorporated by reference: U.S. Pat. Nos. 5,739, 386, 5,700,642 and 5,830,655; and U.S. Patent Publication Nos. 2003/0186226 and 2004/0106728; and in Urdea and Horn, U.S. Pat. No. 5,367,066.

Returning to FIG. 1, in some embodiments, an ordered sequence of nucleotides are coupled to an initiator nucleic acid using a template-free polymerase, such as TdT, in the presence of 3'-O-protected dNTPs in each synthesis step. In some embodiments, the method of synthesizing an oligonucleotide comprises the steps of (a) providing an initiator having a free 3'-hydroxyl; (b) reacting under extension conditions the initiator or an extension intermediate having a free 3'-hydroxyl with a template-free polymerase in the presence of a 3'-O-protected nucleoside triphosphate to produce a 3'-O-protected extension intermediate; (c) depro-
tecting the extension intermediate to produce an extension
intermediate with a free 3'-hydroxyl; and (d) repeating steps
(b) and (c) until the polynucleotide is synthesized. (Some-
times the terms "extension intermediate" or "elongation
fragment" or "growing chain" are used interchangeably). In
some embodiments, an initiator is provided as an oligo-
nucleotide attached to a solid support, e.g. by its 5' end. The
above method may also include washing steps after the
reaction, or extension, step, as well as after the de-protecting
step. For example, the step of reacting may include a
sub-step of removing unincorporated nucleoside triphos-
phates, e.g. by washing, after a predetermined incubation
period, or reaction time. Such predetermined incubation
periods or reaction times may be a few seconds, e.g. 30 sec,
to several minutes, e.g. 30 min.

When the sequence of polynucleotides on a synthesis
support includes reverse complementary subsequences, sec-
ondary intra-molecular or cross-molecular structures may be
created by the formation of hydrogen bonds between the
reverse complementary regions. In some embodiments, base
protecting moieties for exocyclic amines are selected so that
hydrogens of the protected nitrogen cannot participate in
hydrogen bonding, thereby preventing the formation of such
secondary structures. That is, base protecting moieties may
be employed to prevent the formation of hydrogen bonds,
such as are formed in normal base pairing, for example,
between nucleosides A and T and between G and C. At the
end of a synthesis, the base protecting moieties may be
removed and the polynucleotide product may be cleaved
from the solid support, for example, by cleaving it from its
initiator.

In addition to providing 3'-O-blocked dNTP monomers
with base protection groups, elongation reactions may be
performed at higher temperatures using thermal stable tem-
plate-free polymerases. For example, a thermal stable tem-
plate-free polymerase having activity above 40° C. may be
employed; or, in some embodiments, a thermal stable tem-
plate-free polymerase having activity in the range of from
40-85° C. may be employed; or, in some embodiments, a
thermal stable template-free polymerase having activity in
the range of from 40-65° C. may be employed.

In some embodiments, elongation conditions may include
adding solvents to an elongation reaction mixture that inhibit
hydrogen bonding or base stacking. Such solvents include
water miscible solvents with low dielectric constants, such
as dimethyl sulfoxide (DMSO), methanol, and the like.
Likewise, in some embodiments, elongation conditions may
include the provision of chaotropic agents that include, but
are not limited to, n-butanol, ethanol, guanidinium chloride,
lithium perchlorate, lithium acetate, magnesium chloride,
phenol, 2-propanol, sodium dodecyl sulfate, thiourea, urea,
and the like. In some embodiments, elongation conditions
include the presence of a secondary-structure-suppressing
amount of DMSO. In some embodiments, elongation con-
ditions may include the provision of DNA binding proteins
that inhibit the formation of secondary structures, wherein
such proteins include, but are not limited to, single-stranded
binding proteins, helicases, DNA glycolases, and the like.

3'-O-blocked dNTPs without base protection may be
purchased from commercial vendors or synthesized using
published techniques, e.g. U.S. Pat. No. 7,057,026; Guo et
al, Proc. Natl. Acad. Sci., 105(27): 9145-9150 (2008);
Benner, U.S. Pat. Nos. 7,544,794 and 8,212,020; Interna-
tional patent publications WO2004/005667, WO91/06678;
Canard et al, Gene (cited herein); Metzker et al, Nucleic
Acids Research, 22: 4259-4267 (1994); Meng et al, J. Org.

Chem., 14: 3248-3252 (3006); U.S. patent publication 2005/
037991. 3'-O-blocked dNTPs with base protection may be
synthesized as described below.

When base-protected dNTPs are employed the above
method of FIG. 1 may further include a step (e) removing
base protecting moieties, which in the case of acyl or
amidine protection groups may (for example) include treat-
ing with concentrated ammonia.

The above method may also include capping step(s) as
well as washing steps after the reacting, or extending, step,
as well as after the deprotecting step. As mentioned above,
in some embodiments, capping steps may be included in
which non-extended free 3'-hydroxyls are reacted with com-
pounds that prevents any further extensions of the capped
strand. In some embodiments, such compound may be a
dideoxynucleoside triphosphate. In other embodiments,
non-extended strands with free 3'-hydroxyls may be
degraded by treating them with a 3'-exonuclease activity,
e.g. Exo I. For example, see Hyman, U.S. Pat. No. 5,436,
143. Likewise, in some embodiments, strands that fail to be
deblocked may be treated to either remove the strand or
render it inert to further extensions.

In some embodiments, reaction conditions for an elonga-
tion step (also sometimes referred to as an extension step or
a coupling step) may comprising the following: 2.0 µM
purified TdT; 125-600 µM 3'-O-blocked dNTP (e.g. 3'-O—
NH$_2$-blocked dNTP); about 10 to about 500 mM potassium
cacodylate buffer (pH between 6.5 and 7.5) and from about
0.01 to about 10 mM of a divalent cation (e.g. CoCl$_2$ or
MnCl$_2$), where the elongation reaction may be carried out in
a 50 µL reaction volume, at a temperature within the range
RT to 45° C., for 3 minutes. In embodiments, in which the
3'-O-blocked dNTPs are 3'-O—NH$_2$-blocked dNTPs, reac-
tion conditions for a deblocking step may comprise the
following: 700 mM NaNO$_2$; 1 M sodium acetate (adjusted
with acetic acid to pH in the range of 4.8-6.5), where the
deblocking reaction may be carried out in a 504 volume, at
a temperature within the range of RT to 45° C. for 30
seconds to several minutes. Washes may be performed with
the cacodylate buffer without the components of the cou-
pling reaction (e.g. enzyme, monomer, divalent cations).

Depending on particular applications, the steps of
deblocking and/or cleaving may include a variety of chemi-
cal or physical conditions, e.g. light, heat, pH, presence of
specific reagents, such as enzymes, which are able to cleave
a specified chemical bond. Guidance in selecting 3'-O-
blocking groups and corresponding de-blocking conditions
may be found in the following references, which are incor-
porated by reference: Benner, U.S. Pat. Nos. 7,544,794 and
8,212,020; 5,808,045; U.S. patent 8808988; International
patent publication WO91/06678; and references cited below.
In some embodiments, the cleaving agent (also sometimes
referred to as a de-blocking reagent or agent) is a chemical
cleaving agent, such as, for example, dithiothreitol (DTT).
In alternative embodiments, a cleaving agent may be an
enzymatic cleaving agent, such as, for example, a phos-
phatase, which may cleave a 3'-phosphate blocking group. It
will be understood by the person skilled in the art that the
selection of deblocking agent depends on the type of
3'-nucleotide blocking group used, whether one or multiple
blocking groups are being used, whether initiators are
attached to living cells or organisms or to solid supports, and
the like, that necessitate mild treatment. For example, a
phosphine, such as tris(2-carboxyethyl)phosphine (TCEP)
can be used to cleave a 3'O-azidomethyl groups, palladium
complexes can be used to cleave a 3'O-allyl groups, or
sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups may be used in parallel synthesis embodiments. It is understood that other blocking group pairs, or groups containing more than two, may be available for use in these embodiments of the invention.

| | |
|---|---|
| 3'-O-NH2 | 3'-O-azidomethyl |
| 3'-O-NH2 | 3'-O-allyl |
| 3'-O-NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM MgCl$_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3'-phosphate-blocked nucleotides in accordance with the invention are nucleotidyl-3'-phosphate monoester/nucleotidyl-2',3'-cyclic phosphate, nuclcotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte fur Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

—O—Z wherein —Z is any of —C(R')$_2$—O—R", —C(R')$_2$—N (R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')$_2$ represents a group of formula=C(R''')$_2$ wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')$_2$—F, the F is exchanged for OH, SH or NH$_2$, preferably OH, which intermediate dissociates under aqueous conditions to afford a molecule with a free 3'-OH; with the proviso that where Z is —C(R')$_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA)

In a further embodiments, the 3'-blocked nucleotide triphosphate is blocked by either a 3' azidomethyl, 3'-O—NH$_2$ or 3'-O-allyl group.

In still other embodiments, 3'-O-blocking groups of the invention include 3'-O-methyl, 3' (2-nitrobenzyl), 3'-O-allyl, 3'-O-amine, 3'-O-azidomethyl, 3'-O-tert-butoxy ethoxy, 3'-O-(2-cyanoethyl), and 3'-O-propargyl.

In some embodiments, 3'-O- protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

In some embodiments, enzymatic synthesis methods employ TdT variants that display increased incorporation activity with respect to 3'-O-modified nucleoside triphosphates. For example, such TdT variants may be produced using techniques described in Champion et al, U.S. patent Ser. No. 10/435,676, which is incorporated herein by reference. In some embodiments, a TdT variant is employed having an amino acid sequence at least 60 percent identical to SEQ ID NO: 2 and a substitution at a first arginine at position 207 and a substitution at a second arginine at position 325, or functionally equivalent residues thereof. In some embodiments, a terminal deoxynucleotidyl transferase (TdT) variant is employed that has an amino acid sequence at least sixty percent identical to an amino acid sequence selected from SEQ ID NO: 2, 3, 4, 5, 6, 7, 8, 9, 10, 11, 12, 13, 14 or 15 with a substitution of arginine ("first arginine")

embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent homology would be in regard to sequences 1-24, 26-80 and 82-100.

In regard to (ii), such 3'-O-modified nucleotide may comprise a 3'-O-NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the above TdT variants have substitutions at the first and second arginines as shown in Table 1.

TABLE 1

| SEQ ID NO | | | Substitutions | | |
|---|---|---|---|---|---|
| 1 | M192R/Q | C302G/R | R336L/N | R454P/N/A/V | E457N/L/T/S/K |
| 2 | M63R/Q | C173G/R | R207L/N | R325P/N/A/V | E328N/L/T/S/K |
| 3 | M63R/Q | C173G/R | R207L/N | R324P/N/A/V | E327N/L/T/S/K |
| 4 | M63R/Q | C173G/R | R207L/N | R324P/N/A/V | E327N/L/T/S/K |
| 5 | — | C172G/R | R206L/N | R320P/N/A/V | — |
| 6 | M63R/Q | C173G/R | R207L/N | R331P/N/A/V | E334N/L/T/S/K |
| 7 | M63R/Q | C173G/R | R207L/N | — | E328N/L/T/S/K |
| 8 | — | C174G/R | R208L/N | R331P/N/A/V | E334N/L/T/S/K |
| 9 | M73R/Q | C173G/R | R207L/N | R325P/N/A/V | E328N/L/T/S/K |
| 10 | M64R/Q | C174G/R | R208L/N | — | E329N/L/T/S/K |
| 11 | M61R/Q | C171G/R | R205L/N | R323P/N/A/V | E326N/L/T/S/K |
| 12 | M63R/Q | C173G/R | R207L/N | R328P/N/A/V | E331N/L/T/S/K |
| 13 | — | C173G/R | R207L/N | R325P/N/A/V | E328N/L/T/S/K |
| 14 | M63R/Q | C182G/R | R216L/N | R338P/N/A/V | E341N/L/T/S/K |
| 15 | M66R/Q | C176G/R | R210L/N | R328P/N/A/V | E331N/L/T/S/K | at position 207 with respect to SEQ ID NOs 2, 3, 4, 6, 7, 9, 12 and 13, at position 206 with respect to SEQ ID NO 5, at position 208 with respect to SEQ ID NOs 8 and 10, at position 205 with respect to SEQ ID NO 11, at position 216 with respect to SEQ ID NO 14 and at position 210 with respect to SEQ ID NO 15; and a substitution of arginine ("second arginine") at position 325 with respect to SEQ ID NOs 2, 9 and 13, at position 324 with respect to SEQ ID NOs 3 and 4, at position 320 with respect to SEQ ID NO 320, at position 331 with respect to SEQ ID NOs 6 and 8, at position 323 with respect to SEQ ID NO 11, at position 328 with respect to SEQ ID NOs 12 and 15, and at position 338 with respect to SEQ ID NO 14; or functionally equivalent residues thereof; wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some In some embodiments, further TdT variants for use with methods and apparatus of the invention include one or more of the further substitutions of methionine, cysteine or glutamic acid, as shown in Table 1.

Further specific TdT variants that may be used in methods and apparatus of the invention are set forth in Table 2. Each of the TdT variants DS1001 through DS1018 of Table 2 comprises an amino acid sequence at least 60 percent identical to SEQ ID NO 2 and comprises the substitutions at the indicated positions. In some embodiments, TdT variants DS1001 through DS1018 comprises an amino acid sequence at least 80 percent identical to SEQ ID NO 2 and comprises the substitutions at the indicated positions; in some embodiments, TdT variants DS1001 through DS1018 comprises an amino acid sequence at least 90 percent identical to SEQ ID NO 2 and comprises the substitutions at the indicated positions; in some embodiments, TdT variants DS1001 through DS1018 comprises an amino acid sequence at least 95 percent identical to SEQ ID NO 2 and comprises the substitutions at the indicated positions; in some embodiments, TdT variants DS1001 through DS1018 comprises an amino acid sequence at least 97 percent identical to SEQ ID NO 2 and comprises the substitutions at the indicated positions; in some embodiments, TdT variants DS1001 through DS1018 comprises an amino acid sequence at least 98 percent identical to SEQ ID NO 2 and comprises the substitutions at the indicated positions; in some embodiments, TdT variants DS1001 through DS1018 comprises an amino acid sequence at least 99 percent identical to SEQ ID NO 2 and comprises the substitutions at the indicated positions.

Further specific TdT variants that may be used in methods and apparatus of the invention comprise amino acid sequences at least 90 percent identical (or at least 95 percent identical) to SEQ ID NO: 16, 17, 18, 19, 20, 21, 22, 23, 24, 25, 26, 27, 28, 29 or 30 wherein the amino acid sequence of SEQ ID Nos: 16, 17, 18, 19 and 20 each are substituted at position 4 with a stabilizing mutation selected from the group consisting of E, S, D and N, and wherein the TdT variant (i) is capable of synthesizing a nucleic acid fragment without a template and (ii) is capable of incorporating a 3'

TABLE 2

| | Specific TdT Variants for Use with Methods of the Invention |
|---|---|
| DS1001 (TH M27) | A17V + L52F + M63R + A108V + C173G + R207L + K265T + G284P + E289V + R325P + E328N + R351K |
| DS1002 (M44) | A17V + Q37E + D41R + L52F + G57E + M63R + S94R + G98E + A108V + S119A + L131R + S146E + Q149R + C173G + R207L + K265T + G284P + E289V + R325P + Q326F + E328N + H337D + R351K + W377R |
| DS1003 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1004 (M45) | A17V + Q37E + D41R + L52F + G57E + M63R + S94R + G98E + A108V + S146E + Q149R + C173G + F193Y + V199M + M201V + R207L + K265T + G284P + E289V + R325A + Q326F + E328N + R351K |
| DS1005 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1006 (M46) | L52F + A108V + R351K + A17V + Q37E + D41R + G57E+ C59R + L60D + M63R + S94R + G98E + S119A + L131R + S146E + Q149R + C173G + R207L + K265T + G284P + E289V + R325A + Q326F + E328N |
| DS1007 (M47) | L52F + A108V + R351K + A17V + Q37E + D41R + G57E + C59R + L60D + M63R + S94R + G98E + K118Q + S119A + L131R + S146E + Q149R + C173G + R207L + K265T + G284P + E289V + R325A + Q326F + E328N + W377R |
| DS1008 | A17V + Q37E + D41R + L52F + G57E + C59R + L60D + M63R + S94R + G98E + A108V + S119A + L131R + S146E + Q149R + C173G + R207L + F259S + Q261L + G284P + E289V + R325A + Q326F + E328N + R351K + W377R |
| DS1009 (MS 13-34) | A17V + D41R + L53F + G57E + C59R + L60D + M63R + S94R + G98E + K118Q + S119A + L131R + S146E + Q149R + C173G + R207L + K265T + G284P + E289V + R325A + Q326F + R351K + W377R |
| DS1010 (MS 34-1) | A17V + D41R + L52F + G57E + C59R + L60D + M63R + S94R + G98E + A108V + S119A + L131R + S146E + Q149R + R207L + K265T + G284P + E289V + R325A + Q326F + R351K |
| DS1011 | A17V + D41R + L53F + G57E + C59R + L60D + M63R + S94R + G98E + K118Q + S119A + L131R + S146E + Q149R + C173G + R207L + K265T + G284P + E289V + Q326F + R351K + W377R |
| DS1012 (M48) | A17V + Q37E + D41R + L52F + G57E + C59R + L60D + M63R + S94R + G98E + A108V + S119A + L131R + S146E + Q149R + C173G + R207L + F259S + Q261L, G284P + E289V + R325A + Q326F + E328N + R351K + W377R |
| DS1013 | A17V + Q37E + D41R + L52F + G57E + M63R + S94R + G98E + A108V + S146E + Q149R + C173G + R207L + K265T + G284P + E289V + R325A + Q326F + E328N + R351K |
| DS1014 (M49) | A17V + Q37E + D41R + L52F + G57E + C59R + L60D + M63R + S94R + G98E + A108V + S119A + L131R + S146E + Q149R + C173G + R207L + E257D + F259S + K260R + Q261L + G284P + E289V + R325A + Q326F + E328N + R351K + W377R |
| DS1015 | A17V + Q37E + D41R + L52F + G57E + C59R + L60D + M63R + S94R + G98E + A108V + S119A + L131R + S146E + Q149R + C173G + F193Y + V199M + M201V + R207L + E257D + F259S + K260R + Q261L + G284P + E289V + R325A + Q326F + E328N + R351K + W377R |
| DS1016 TH c2_5 | A17V + D41R + L52F + G57E + M63R + S94R + G98E + A108V + S146E + Q149R + C173G + M184T + R207L + K209H + G284L + E289A + R325V + E328K + R351K |
| DS1017 (M27) | A17V + L52F + G57E + M63R + A108V + C173G + R207L + K265T + G284P + E289V + R325P + E328N + R351K |
| DS1018 (M60) | A17V + L32T + Q37R + D41R + L52F + G57E + C59R + L60D + M63R + S67A + S94R + G98E + A108V + S119A +L131R + S146E + Q149R + V171A + S172E + C173R + V182I + S183E + R207L + K209H + M210K + T211I + E223G + A224P + E228D + Q261L + G284P + E289V + R325A + Q326F + E328N + R351K + D372E | protected-nucleotide onto a free 3'-hydroxyl of a polynucleotide. In further embodiments, such stabilizing mutation at position 4 is E.

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 3A.

TABLE 3A

| Synonymous Sets of Amino Acids I | |
| --- | --- |
| Amino Acid | Synonymous Set |
| Ser | Ser, Thr, Gly, Asn |
| Arg | Arg, Gin, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gin, Thr, Arg |
| Gln | Gin, Glu, Lys, Asn, His, Thr, Arg |
| Asn | Asn, Gln, Asp, Ser |
| Lys | Lys, Glu, Gin, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 3B.

TABLE 3B

| Synonymous Sets of Amino Acids II | |
| --- | --- |
| Amino Acid | Synonymous Set |
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gin, Glu, His |
| Asn | Asn, Asp |
| Lys | Lys, Arg |
| Asp | Asp, Asn |

TABLE 3B-continued

| Synonymous Sets of Amino Acids II | |
| --- | --- |
| Amino Acid | Synonymous Set |
| Glu | Glu, Gin |
| Met | Met, Phe, Ile, Val, Leu |
| Trp | Trp |

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999).

"Functionally equivalent" in reference to amino acid positions in two or more different TdTs means (i) the amino acids at the respective positions play the same functional role in an activity of the TdTs, and (ii) the amino acids occur at homologous amino acid positions in the amino acid sequences of the respective TdTs. It is possible to identify positionally equivalent or homologous amino acid residues in the amino acid sequences of two or more different TdTs on the basis of sequence alignment and/or molecular modelling. In some embodiments, functionally equivalent amino acid positions belong to inefficiency motifs that are conserved among the amino acid sequences of TdTs of evolutionarily related species, e.g. genus, families, or the like. Examples of such conserved inefficiency motifs are described in Motea et al, Biochim. Biophys. Acta. 1804(5): 1151-1166 (2010); Delarue et al, EMBO J., 21: 427-439 (2002); and like references.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Kornberg and Baker, DNA Replication, Second Edition (W.H. Freeman, 1992), or like reference. Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms' usage.

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http:// blast.ncbi.nlm nih.gov/or ttp://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methyllysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

40

The invention claimed is:

1. A method for synthesizing with a template-free polymerase a plurality of polynucleotides each with a predetermined sequence, wherein the template-free polymerase has reduced coupling efficiency at one or more inefficiency motifs, the method comprising the steps of:

(a) providing a reaction chamber for each polynucleotide of the plurality of polynucleotides, each reaction chamber having disposed therein a synthesis support with initiators attached, wherein each initiator has a free 3'-hydroxyl, and wherein each reaction chamber has an inlet and an outlet and a filter that retains the synthesis support and that is operationally associated with the outlet so that reaction solutions exiting the reaction chamber pass through the filter;

(b) providing a waste manifold operationally associated with the outlets of the reaction chambers so that whenever a positive pressure differential is created between the reaction chambers and the waste manifold, reaction solutions are removed from the reaction chambers;

(c) repeating for each reaction chamber, until a polynucleotide of such reaction chamber is complete, cycles of the following reaction steps:

(i) contacting in a coupling solution the initiator or a deprotected elongated fragment with a 3'-protected nucleoside triphosphate and a template-free polymerase so that the initiator or the deprotected elongated fragment is elongated by the 3'-protected nucleoside triphosphate to form a 3'-protected elongated fragment, (ii) deprotecting the 3'-protected elongated fragment with a deprotection solution, and (iii) applying a pressure differential between the reaction chambers and the waste manifold to remove reaction solution(s) from the reaction chambers;

wherein the kind of 3'-protected nucleoside triphosphate contacted in step (i) in a reaction chamber is determined by the predetermined sequence of the reaction chamber, and wherein, prior to each cycle, one or more short cycles of step (i) is carried out in a reaction chamber whenever an inefficiency motif is present at a 3' end of the deprotected elongated fragment of such reaction chamber, wherein the inefficiency motif is CCA, CTA, GCA, GTA or CCT.

2. The method of claim 1, wherein said cycles and said short cycles have the same duration.

3. The method of claim 1, further including a step of cleaving said polynucleotides from said synthesis supports.

4. The method of claim 1, wherein said template-free polymerase is a terminal deoxynucleotidyl transferase (TdT).

5. The method of claim 4, wherein said TdT is a TdT variant having an amino acid sequence at least 90 percent identical to SEQ ID NO: 21, 22, 23, 24, 25, 26, 27, 28, 29 or 30, or an amino acid sequence at least 90 percent identical to SEQ ID NO: 16, 17, 18, 19, or 20 and having a Q4E/S/D/N substitution, wherein the TdT variant (i) is capable of synthesizing a nucleic acid fragment without a template, and (ii) is capable of incorporating a 3'-O-protected-nucleotide onto a free 3'-hydroxyl of a polynucleotide.

6. The method of claim 1, wherein protease treatment is performed either in each cycle or periodically during the synthesis process.

7. The method of claim 1, further comprising, after completing the synthesis of the polynucleotides, (i) cleaving the completed polynucleotides from the solid supports, and (ii) purifying the completed polynucleotides.

8. The method of claim 7, wherein the cleaving and the purifying are performed in the reaction chambers.

9. The method of claim 7, wherein the polynucleotides still attached to the solid supports are transferred to other reaction vessels for the cleaving and the purifying.

\*    \*    \*    \*    \*